(12) United States Patent
Vitek et al.

(10) Patent No.: US 12,402,802 B2
(45) Date of Patent: Sep. 2, 2025

(54) AVOIDING MRI-INTERFERENCE WITH CO-EXISTING SYSTEMS

(71) Applicants: Shuki Vitek, Haifa (IL); Benny Assif, Ramat Hasharon (IL); Adi Greenberg, Haifa (IL)

(72) Inventors: Shuki Vitek, Haifa (IL); Benny Assif, Ramat Hasharon (IL); Adi Greenberg, Haifa (IL)

(73) Assignee: INSIGHTEC LTD., Tirat Carmel (IL)

( * ) Notice: Subject to any disclaimer, the term of this patent is extended or adjusted under 35 U.S.C. 154(b) by 1024 days.

(21) Appl. No.: 17/210,859

(22) Filed: Mar. 24, 2021

(65) Prior Publication Data

US 2021/0204830 A1 Jul. 8, 2021

Related U.S. Application Data

(63) Continuation-in-part of application No. 15/979,602, filed on May 15, 2018, now abandoned, which is a continuation of application No. 13/222,086, filed on Aug. 31, 2011, now abandoned.

(51) Int. Cl.
| | |
|---|---|
| *A61B 5/00* | (2006.01) |
| *A61B 5/055* | (2006.01) |
| *A61N 7/02* | (2006.01) |
| *A61B 8/08* | (2006.01) |
| *A61B 17/22* | (2006.01) |
| *A61B 90/00* | (2016.01) |
| *A61N 7/00* | (2006.01) |

(52) U.S. Cl.
CPC ............... *A61B 5/055* (2013.01); *A61N 7/02* (2013.01); *A61B 8/0808* (2013.01); *A61B 2017/22007* (2013.01); *A61B 2090/374* (2016.02); *A61B 2090/378* (2016.02); *A61N 2007/0078* (2013.01)

(58) Field of Classification Search
CPC ....................................................... A61B 5/055
See application file for complete search history.

(56) References Cited

U.S. PATENT DOCUMENTS

| | | | |
|---|---|---|---|
| 2,795,709 A | 6/1957 | Camp | |
| 3,142,035 A | 7/1964 | Harris | |
| 3,942,150 A | 3/1976 | Booth et al. | |
| 3,974,475 A | 8/1976 | Burckhardt et al. | |
| 3,992,693 A | 11/1976 | Martin et al. | |

(Continued)

FOREIGN PATENT DOCUMENTS

| | | |
|---|---|---|
| DE | 4345308 C2 | 2/2001 |
| DE | 10102317 A1 | 8/2002 |

(Continued)

OTHER PUBLICATIONS

"Progress in Multimodality Imaging: Truly Simultaneous Ultrasound and Magnetic Resonance Imaging" IEEE transactions vol. 26, No. 12, Dec. 2007). (Year: 2007).*

(Continued)

*Primary Examiner* — Joseph M Santos Rodriguez
(74) *Attorney, Agent, or Firm* — Morgan, Lewis & Bockius LLP

(57) ABSTRACT

MRI interference with a co-existing ultrasound system may be reduced or avoided by carrying out RF-sensitive operations of the treatment system only when gradient field activity of the MRI system is suppressed.

17 Claims, 14 Drawing Sheets

(56) References Cited

U.S. PATENT DOCUMENTS

| | | |
|---|---|---|
| 4,000,493 A | 12/1976 | Spaulding et al. |
| 4,074,564 A | 2/1978 | Anderson |
| 4,206,653 A | 6/1980 | Lemay |
| 4,339,952 A | 7/1982 | Foster |
| 4,454,597 A | 6/1984 | Sullivan |
| 4,478,083 A | 10/1984 | Hassler et al. |
| 4,505,156 A | 3/1985 | Questo |
| 4,526,168 A | 7/1985 | Hassler et al. |
| 4,537,074 A | 8/1985 | Dietz |
| 4,549,533 A | 10/1985 | Cain et al. |
| 4,554,925 A | 11/1985 | Young |
| 4,636,964 A | 1/1987 | Jacobs et al. |
| 4,662,222 A | 5/1987 | Johnson |
| 4,858,597 A | 8/1989 | Kurtze et al. |
| 4,865,042 A | 9/1989 | Umemura et al. |
| 4,888,746 A | 12/1989 | Wurster et al. |
| 4,889,122 A | 12/1989 | Watmough et al. |
| 4,893,284 A | 1/1990 | Magrane |
| 4,893,624 A | 1/1990 | Lele |
| 4,937,767 A | 6/1990 | Reuschel et al. |
| 5,209,221 A | 5/1993 | Riedlinger |
| 5,211,160 A | 5/1993 | Talish et al. |
| 5,247,935 A | 9/1993 | Cline et al. |
| 5,271,400 A | 12/1993 | Dumoulin et al. |
| 5,275,165 A | 1/1994 | Ettinger et al. |
| 5,291,890 A | 3/1994 | Cline et al. |
| 5,307,812 A | 5/1994 | Hardy et al. |
| 5,307,816 A | 5/1994 | Hashimoto et al. |
| 5,318,025 A | 6/1994 | Dumoulin et al. |
| 5,323,779 A | 6/1994 | Hardy et al. |
| 5,327,884 A | 7/1994 | Hardy et al. |
| 5,329,930 A | 7/1994 | Thomas, III et al. |
| 5,339,282 A | 8/1994 | Kuhn et al. |
| 5,368,031 A | 11/1994 | Cline et al. |
| 5,368,032 A | 11/1994 | Cline et al. |
| 5,379,642 A | 1/1995 | Reckwerdt et al. |
| 5,391,140 A | 2/1995 | Schaetzle et al. |
| 5,413,550 A | 5/1995 | Castel |
| 5,435,312 A | 7/1995 | Spivey et al. |
| 5,443,068 A | 8/1995 | Cline et al. |
| 5,474,071 A | 12/1995 | Chapelon et al. |
| 5,485,839 A | 1/1996 | Aida et al. |
| 5,490,840 A | 2/1996 | Uzgiris et al. |
| 5,507,790 A | 4/1996 | Weiss |
| 5,520,188 A | 5/1996 | Hennige et al. |
| 5,526,814 A | 6/1996 | Cline et al. |
| 5,532,594 A | 7/1996 | Cory et al. |
| 5,549,638 A | 8/1996 | Burdette |
| 5,553,618 A | 9/1996 | Suzuki et al. |
| 5,557,438 A | 9/1996 | Schwartz et al. |
| 5,573,497 A | 11/1996 | Chapelon |
| 5,582,578 A | 12/1996 | Zhong et al. |
| 5,590,653 A | 1/1997 | Aida et al. |
| 5,590,657 A | 1/1997 | Cain et al. |
| 5,601,526 A | 2/1997 | Chapelon et al. |
| 5,605,154 A | 2/1997 | Ries et al. |
| 5,617,371 A | 4/1997 | Williams |
| 5,617,857 A | 4/1997 | Chader et al. |
| 5,643,179 A | 7/1997 | Fujimoto |
| 5,662,170 A | 9/1997 | Donovan et al. |
| 5,665,054 A | 9/1997 | Dory |
| 5,666,954 A | 9/1997 | Chapelon et al. |
| 5,676,673 A | 10/1997 | Ferre et al. |
| 5,687,729 A | 11/1997 | Schaetzle |
| 5,694,936 A | 12/1997 | Fujimoto et al. |
| 5,711,300 A | 1/1998 | Schneider et al. |
| 5,722,411 A | 3/1998 | Suzuki et al. |
| 5,739,625 A | 4/1998 | Falcus |
| 5,743,863 A | 4/1998 | Chapelon |
| 5,752,515 A | 5/1998 | Jolesz et al. |
| 5,759,162 A | 6/1998 | Oppelt et al. |
| 5,762,616 A | 6/1998 | Talish |
| 5,769,790 A | 6/1998 | Watkins et al. |
| 5,810,008 A | 9/1998 | Dekel et al. |
| 5,817,036 A | 10/1998 | Anthony et al. |
| 5,831,739 A | 11/1998 | Ota |
| 5,873,845 A | 2/1999 | Cline et al. |
| 5,897,495 A | 4/1999 | Aida et al. |
| 5,938,600 A | 8/1999 | Van et al. |
| 5,938,608 A | 8/1999 | Bieger et al. |
| 5,947,900 A | 9/1999 | Derbyshire et al. |
| 5,984,881 A | 11/1999 | Shibashi et al. |
| 6,004,269 A | 12/1999 | Crowley et al. |
| 6,023,636 A | 2/2000 | Wendt et al. |
| 6,042,556 A | 3/2000 | Beach et al. |
| 6,071,239 A | 6/2000 | Cribbs et al. |
| 6,113,558 A | 9/2000 | Rosenschein et al. |
| 6,113,559 A | 9/2000 | Klopotek |
| 6,128,522 A | 10/2000 | Acker et al. |
| 6,128,958 A | 10/2000 | Cain |
| 6,148,225 A | 11/2000 | Kestler et al. |
| 6,188,923 B1 | 2/2001 | Bechtold |
| 6,193,659 B1 | 2/2001 | Ramamurthy et al. |
| 6,242,915 B1 | 6/2001 | Hurd |
| 6,246,896 B1 | 6/2001 | Dumoulin et al. |
| 6,263,230 B1 | 7/2001 | Haynor et al. |
| 6,267,734 B1 | 7/2001 | Ishibashi et al. |
| 6,289,233 B1 | 9/2001 | Dumoulin et al. |
| 6,309,355 B1 | 10/2001 | Cain et al. |
| 6,317,619 B1 | 11/2001 | Boemert et al. |
| 6,322,527 B1 | 11/2001 | Talish |
| 6,334,846 B1 | 1/2002 | Ishibashi et al. |
| 6,374,132 B1 | 4/2002 | Acker et al. |
| 6,392,330 B1 | 5/2002 | Zloter et al. |
| 6,397,094 B1 | 5/2002 | Ludeke et al. |
| 6,413,216 B1 | 7/2002 | Cain et al. |
| 6,419,648 B1 | 7/2002 | Vitek et al. |
| 6,424,597 B1 | 7/2002 | Bolomey et al. |
| 6,425,867 B1 | 7/2002 | Vaezy et al. |
| 6,428,532 B1 | 8/2002 | Doukas et al. |
| 6,461,314 B1 | 10/2002 | Pant et al. |
| 6,475,150 B2 | 11/2002 | Haddad |
| 6,478,739 B1 | 11/2002 | Hong |
| 6,501,978 B2 | 12/2002 | Wagshul et al. |
| 6,506,154 B1 | 1/2003 | Ezion et al. |
| 6,506,171 B1 | 1/2003 | Vitek et al. |
| 6,511,428 B1 | 1/2003 | Azuma et al. |
| 6,522,142 B1 | 2/2003 | Freundlich |
| 6,523,272 B1 | 2/2003 | Morales |
| 6,554,826 B1 | 4/2003 | Deardorff |
| 6,559,644 B2 | 5/2003 | Froundlich et al. |
| 6,566,878 B1 | 5/2003 | Komura et al. |
| 6,582,381 B1 | 6/2003 | Yehezkeli et al. |
| 6,599,256 B1 | 7/2003 | Acker et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,618,608 B1 | 9/2003 | Watkins et al. |
| 6,618,620 B1 | 9/2003 | Freundlich et al. |
| 6,626,854 B2 | 9/2003 | Friedman et al. |
| 6,626,855 B1 | 9/2003 | Weng et al. |
| 6,629,929 B1 | 10/2003 | Jago et al. |
| 6,645,162 B2 | 11/2003 | Friedman et al. |
| 6,652,461 B1 | 11/2003 | Levkovitz |
| 6,666,833 B1 | 12/2003 | Friedman et al. |
| 6,676,601 B1 | 1/2004 | Lacoste et al. |
| 6,679,855 B2 | 1/2004 | Horn et al. |
| 6,705,994 B2 | 3/2004 | Vortman et al. |
| 6,719,694 B2 | 4/2004 | Weng et al. |
| 6,733,450 B1 | 5/2004 | Alexandrov et al. |
| 6,735,461 B2 | 5/2004 | Vitek et al. |
| 6,761,891 B1 | 7/2004 | Simon et al. |
| 6,770,031 B2 | 8/2004 | Hynynen et al. |
| 6,770,039 B2 | 8/2004 | Zhong et al. |
| 6,788,619 B2 | 9/2004 | Calvert |
| 6,790,180 B2 | 9/2004 | Vitek |
| 6,824,516 B2 | 11/2004 | Batten et al. |
| 6,951,540 B2 | 10/2005 | Ebbini et al. |
| 6,961,606 B2 | 11/2005 | DeSilets et al. |
| 7,001,379 B2 | 2/2006 | Behl et al. |
| 7,077,820 B1 | 7/2006 | Kadziauskas et al. |
| 7,094,205 B2 | 8/2006 | Marmarelis |
| 7,128,711 B2 | 10/2006 | Medan et al. |
| 7,155,271 B2 | 12/2006 | Halperin et al. |

(56) References Cited

U.S. PATENT DOCUMENTS

| | | |
|---|---|---|
| 7,175,596 B2 | 2/2007 | Vitek et al. |
| 7,175,599 B2 | 2/2007 | Hynynen et al. |
| 7,259,560 B2 | 8/2007 | Yamanaka |
| 7,264,592 B2 | 9/2007 | Shehada |
| 7,264,597 B2 | 9/2007 | Cathignol |
| 7,267,650 B2 | 9/2007 | Chow et al. |
| 7,344,509 B2 | 3/2008 | Hynynen et al. |
| 7,377,900 B2 | 5/2008 | Vitek et al. |
| 7,452,357 B2 | 11/2008 | Vlegele et al. |
| 7,462,488 B2 | 12/2008 | Madsen et al. |
| 7,505,805 B2 | 3/2009 | Kuroda |
| 7,505,808 B2 | 3/2009 | Anderson et al. |
| 7,510,536 B2 | 3/2009 | Foley et al. |
| 7,511,501 B2 | 3/2009 | Wexler |
| 7,535,794 B2 | 5/2009 | Prus et al. |
| 7,553,284 B2 | 6/2009 | Vaitekunas |
| 7,603,162 B2 | 10/2009 | Danz et al. |
| 7,611,462 B2 | 11/2009 | Vortman et al. |
| 7,652,410 B2 | 1/2010 | Prus |
| 7,699,780 B2 | 4/2010 | Vitek et al. |
| 2001/0031922 A1 | 10/2001 | Weng et al. |
| 2001/0049474 A1 | 12/2001 | Wagshul |
| 2002/0035779 A1 | 3/2002 | Krieg et al. |
| 2002/0082589 A1 | 6/2002 | Friedman et al. |
| 2002/0188229 A1 | 12/2002 | Ryaby et al. |
| 2003/0004439 A1 | 1/2003 | Pant et al. |
| 2003/0060820 A1 | 3/2003 | Maguire et al. |
| 2003/0187371 A1 | 10/2003 | Vortman et al. |
| 2003/0199755 A1 | 10/2003 | Halperin |
| 2004/0030227 A1 | 2/2004 | Littrup et al. |
| 2004/0030251 A1 | 2/2004 | Ebbini et al. |
| 2004/0068186 A1 | 4/2004 | Ishida et al. |
| 2004/0122323 A1 | 6/2004 | Vortman et al. |
| 2004/0147919 A1 | 7/2004 | Behl et al. |
| 2004/0199068 A1 | 10/2004 | Bucholz et al. |
| 2004/0210134 A1 | 10/2004 | Hynynen et al. |
| 2004/0236253 A1 | 11/2004 | Vortman et al. |
| 2004/0263172 A1 | 12/2004 | Gray et al. |
| 2004/0267126 A1 | 12/2004 | Takeuchi |
| 2005/0033201 A1 | 2/2005 | Takahashi et al. |
| 2005/0096542 A1 | 5/2005 | Weng et al. |
| 2005/0131301 A1 | 6/2005 | Peszynski et al. |
| 2005/0203444 A1 | 9/2005 | Schonenberger et al. |
| 2005/0240126 A1 | 10/2005 | Foley et al. |
| 2005/0251046 A1 | 11/2005 | Yamamoto et al. |
| 2006/0052661 A1 | 3/2006 | Gannot et al. |
| 2006/0052701 A1 | 3/2006 | Carter et al. |
| 2006/0052706 A1 | 3/2006 | Hynynen et al. |
| 2006/0058671 A1 | 3/2006 | Vitek et al. |
| 2006/0058678 A1 | 3/2006 | Vitek et al. |
| 2006/0079773 A1 | 4/2006 | Mourad et al. |
| 2006/0106300 A1 | 5/2006 | Seppenwoolde et al. |
| 2006/0173385 A1 | 8/2006 | Lidgren et al. |
| 2006/0184069 A1 | 8/2006 | Vaitekunas |
| 2006/0206105 A1 | 9/2006 | Chopra et al. |
| 2006/0229594 A1 | 10/2006 | Francischelli et al. |
| 2007/0016013 A1 | 1/2007 | Camus |
| 2007/0016039 A1 | 1/2007 | Vortman et al. |
| 2007/0055140 A1 | 3/2007 | Kuroda |
| 2007/0066897 A1 | 3/2007 | Sekins et al. |
| 2007/0073135 A1 | 3/2007 | Lee et al. |
| 2007/0098232 A1 | 5/2007 | Matula et al. |
| 2007/0167781 A1 | 7/2007 | Vortman et al. |
| 2007/0197918 A1 | 8/2007 | Vitek et al. |
| 2007/0219470 A1 | 9/2007 | Talish et al. |
| 2008/0027342 A1 | 1/2008 | Rouw et al. |
| 2008/0031090 A1 | 2/2008 | Prus et al. |
| 2008/0033278 A1 | 2/2008 | Assif |
| 2008/0082026 A1 | 4/2008 | Schmidt et al. |
| 2008/0108900 A1 | 5/2008 | Lee et al. |
| 2008/0183077 A1 | 7/2008 | Moreau-Gobard et al. |
| 2008/0228081 A1 | 9/2008 | Becker et al. |
| 2008/0249408 A1 | 10/2008 | Palmeri et al. |
| 2008/0292194 A1 | 11/2008 | Schmidt et al. |
| 2008/0312562 A1 | 12/2008 | Routh et al. |
| 2009/0088623 A1 | 4/2009 | Vortman et al. |
| 2009/0096450 A1 | 4/2009 | Roland |
| 2009/0163980 A1 | 6/2009 | Stevenson |
| 2009/0236333 A1 | 9/2009 | Ben-Shmuel et al. |
| 2010/0056962 A1 | 3/2010 | Vortman et al. |
| 2010/0253347 A1 | 10/2010 | Habara et al. |
| 2011/0034800 A1 | 2/2011 | Vitek et al. |

FOREIGN PATENT DOCUMENTS

| | | |
|---|---|---|
| EP | 151073 A2 | 8/1985 |
| EP | 1132054 A1 | 9/2001 |
| EP | 1582886 A1 | 10/2005 |
| EP | 1774920 A1 | 4/2007 |
| EP | 1790384 A1 | 5/2007 |
| FR | 2649002 A1 | 1/1991 |
| FR | 2806611 A1 | 9/2001 |
| JP | 11-313833 A | 11/1999 |
| WO | WO1991/000059 A1 | 1/1991 |
| WO | WO1998/052465 A1 | 11/1998 |
| WO | WO2000/031614 A1 | 6/2000 |
| WO | WO2001/043640 A1 | 6/2001 |
| WO | WO2001/050156 A1 | 7/2001 |
| WO | WO2001/058337 A2 | 8/2001 |
| WO | WO2001/066189 A1 | 9/2001 |
| WO | WO2001/080709 A2 | 11/2001 |
| WO | WO2002/058791 A1 | 8/2002 |
| WO | WO2003/013654 A1 | 2/2003 |
| WO | WO2003/070105 A1 | 8/2003 |
| WO | WO2003/097162 A2 | 11/2003 |
| WO | WO2003/098232 A2 | 11/2003 |
| WO | WO2004/093686 A1 | 11/2004 |
| WO | WO2005/058029 A2 | 6/2005 |
| WO | WO2006/018837 A2 | 2/2006 |
| WO | WO2006/025001 A1 | 3/2006 |
| WO | WO2006/087649 A1 | 8/2006 |
| WO | WO2006/119572 A1 | 11/2006 |
| WO | WO2007/073551 A1 | 6/2007 |
| WO | WO2007/093998 A1 | 8/2007 |
| WO | WO2008/039449 A1 | 4/2008 |
| WO | WO2008/050278 A1 | 5/2008 |
| WO | WO2008/075203 A2 | 6/2008 |
| WO | WO2008/119054 A1 | 10/2008 |
| WO | WO2009/044276 A2 | 4/2009 |
| WO | WO2009/055587 A1 | 4/2009 |
| WO | WO2009/094554 A2 | 7/2009 |
| WO | WO2011/015949 A1 | 2/2011 |

OTHER PUBLICATIONS

"Abstract", Focus Surgery, available online at <http://www.focus-surgery.com/Sanghvi.hlm> retrieved on Jan. 3, 2003, 2002, 1 page.

"FDA Approves Exablate 2000 as Non-invasive surgery for Fibroids", Oct. 22, 2004, 4 pages.

"How does HIFU Create a Lesion?", available online at <http://www.edaphifu.com/eno/physicians/hifu/2d_hifu_lesion.him>, retrieved on Jan. 3, 2003, 2002, 1 page.

"MR Guided Focused Ultrasound; Non-Invasive Surgery for Uterine Fibroids", ExAblate 2000, InSightec, Ltd., 2000, 2 pages.

"Prostate Cancer Phase 1 Clinical Trials Using High Intensity Focused Ultrasound (HIFU)", Focus Surgery, available Jnline at <http://www.focus-surgery.com/PCT%20Treatmen1%20wilh%20HIEU.hlm> retrieved on Jan. 3, 2003, 2002, 2 pages.

"What are the Physical Principles?", available online at <http://www.edaphifu.com/eng/physicians/ hifu/2c hifu_physical.hlm>, retrieved on Jan. 3, 2003, 2 pages.

"What is HIFU? HIFU: High Intensity Focused Ultrasound", available online at <http://www.edaphifu.com/eno/ Jhvsicians/hifu2a_hifu overview.him>, retrieved on Jan. 3, 2003, 1 page.

Examination Report in Chinese Patent Application No. 200880109807.1, mailed Dec. 26, 2011, 13 pages.

International Application Serial No. PCT/IB2003/005551, International Search Report mailed Mar. 9, 2004, 3 pages.

International Application Serial No. PCT/IB2003/005551, International Written Opinion mailed on Sep. 10, 2004.

(56) References Cited

OTHER PUBLICATIONS

International Application Serial No. PCT/IB2004/001498, International Search Report and Written Opinion mailed Aug. 31, 2004, 8 pages.
International Application Serial No. PCT/IB2004/001512, International Preliminary Report mailed on Nov. 25, 2005, 5 pages.
International Application Serial No. PCT/IB2005/002273, International Search Report and Written Opinion mailed on Dec. 20, 2005, 6 pages.
International Application Serial No. PCT/IB2005/002413, International Search Report and Written Opinion mailed Nov. 22, 2005, 8 pages.
International Application Serial No. PCT/IB2006/001641, International Search Report and Written Opinion mailed Sep. 25, 2006, 8 pages.
International Application Serial No. PCT/IB2006/003300, International Search Report and Written Opinion mailed on Feb. 14, 2008, 7 pages.
International Application Serial No. PCT/IB2007/001079, International Search Report and Written Opinion mailed on Dec. 10, 2007, 11 pages.
International Application Serial No. PCT/IB2007/001079, Partial International Search Report and Written Opinion mailed on Sep. 25, 2007.
International Application Serial No. PCT/IB2007/002134, International Search Report and Written Opinion mailed on Dec. 13, 2007, 8 pages.
International Application Serial No. PCT/IB2007/002140, International Search Report and Written Opinion mailed on Dec. 29, 2008, 7 pages.
International Application Serial No. PCT/IB2008/003069, International Preliminary Report on Patentability mailed on Apr. 15, 2010, 8 pages.
International Application Serial No. PCT/IB2008/003069, International Search Report and Written Opinion mailed on Apr. 27, 2009, 10 pages.
International Application Serial No. PCT/IB2010/000189, International Search Report and Written Opinion mailed on Jun. 1, 2010, 11 pages.
International Application Serial No. PCT/IB2010/000971, International Search Report and Written Opinion mailed on Jul. 29, 2010, 9 pages.
International Application Serial No. PCT/IB2010/044345, International Search Report and Written Opinion mailed on Dec. 2, 2010, 11 pages.
International Application Serial No. PCT/ IB12/002115, International Preliminary Report on Patentability mailed on Mar. 13, 2014, 6 pages.
International Application Serial No. PCT/IL2001/000340, International Written Opinion mailed on Feb. 24, 2003.
International Application Serial No. PCT/IL2002/000477, International Written Opinion mailed on Feb. 25, 2003, 9 pages.
International Search Report and Written Opinion for International Application No. PCT/IB2012/002115 issued on Jan. 17, 2013 and mailed on Jan. 25, 2013.
Botros et al., "A Hybrid Computational Model for Ultrasound Phased-Array Heating in Presence of Strongly Scattering Obstacles", IEEE Trans Biomed Eng., vol. 44, No. 11, Nov. 1997, pp. 1039-1050.
Cain et al., "Concentric-Ring and Sector-Vortex Phased-Array Applicators for Ultrasound Hyperthermia", IEEE Transactions on Microwave Theory and Techniques, vol. MTI-34, No. 5, May 1986, pp. 542-551.
Chen et al., "MR Acoustic Radiation Force Imaging: Comparison of Encoding Gradients", Proc. Intl. Soc. Mag. Reson. Med. vol. 16, 2008, p. 1240.
Cline et al., "Focused US System for MR Imaging-Guide Tumor Ablation", Radiology, vol. 194, No. 3, Mar. 1995, pp. 731-737.

Cline et al., "MR Temperature Mapping of Focused Ultrasound Surgery", Magnetic Resonance in Medicine, vol. 31, 1994, pp. 628-636.
Cline et al., "Simultaneous Magnetic Resonance Phase and Magnitude Temperature Maps in Muscle", Magnetic Resonance in Medicine, vol. 35, No. 3, Mar. 1996, pp. 309-315.
Curiel, L. et al., "Progress in Multimodality Imaging: Truly Simultaneous Ultrasound and Magnetic Resonance Imaging", IEEE Transactions on Medical Imaging, IEEE Service Center, Piscataway, NJ, US, vol. 26, No. 12, Dec. 1, 2007 (Dec. 1, 2007), pp. 1710-1746.
Daum et al., "Design and Evaluation of a Feedback Based Phased Array System for Ultrasound Surgery", IEEE Transactions on Ultrasonics, Ferroelectrics and Frequency Control, vol. 45, No. 2, Mar. 1998, pp. 431-438.
Delannoy, J. et al., "Hyperthermia System Combined with a Magnetic Resonance Imaging Unit", Medical Physics, AIP, Melville, NY, US, vol. 17, No. 5, Sep. 1, 1990 (Sep. 1, 1990), pp. 855-860.
De Senneville et al., "Real-Time Adaptive Methods for Treatment of 1 Mobile Organs by MRI-Controlled High-Intensity Focused Ultrasound", Magnetic Resonance in Medicine, vol. 57, Feb. 2007, pp. 319-330.
Edap, "How is Ablatherm Treatment Performed?", available online at <http://www.edaphifu.com/eno/physicians/ hifu/3c treatment treat-description.him>, accessed Jan. 3, 2003, 2002, 3 pages.
Fjield et al., "The Combined Concentric—Ring and Sector-Vortex Phased Array for MRI Guided Ultrasound Surgery", IEEE Transactions on Ultrasonics, Ferroelectrics and Frequency Control, vol. 44, No. 5, Sep. 1997, pp. 1157-1167.
Herbert et al., "Energy-Based Adaptive Focusing of Waves: Application to Ultrasonic Transcranial Therapy", 8th International Symposium on Therapeutic Ultrasound, vol. 1113, Sep. 2008, 3 pages.
Huber et al., "A New Noninvasive Approach in Breast Cancer Therapy Using Magnetic Resonance Imaging-guided Focused Ultrasound Surgery", Cancer Research, vol. 61, Dec. 2001, pp. 8441-8447.
Jolesz et al., "Integration of Interventional MRI with Computer-Assisted Surgery", Journal of Magnetic Resonance Imaging, vol. 13, No. 1, Special Issue: Interventional MRI, Part 2, Jan. 2001, pp. 69-77.
Kohler et al., "Volumetric HIFU Ablation Guided by Multiplane MRI Thermometry", 8th International Symposium on Therapeutic Ultrasound, Minneapolis (Minnesota), USA, Sep. 2009, pp. 228-230.
Kowalski et al., "Optimization of Electromagnetic Phased-Arrays for Hyperthermia via Magnetic Resonance Temperature Estimation", IEEE Transactions on Biomedical Engineering, vol. 49, No. 11, Nov. 2002, pp. 1229-1241.
Maxwell et al., "Noninvasive Thrombolysis using Pulsed Ultrasound Cavitation Therapy-Histotripsy", Ultrasound Med. Biol., vol. 35, No. 12, Dec. 2009, pp. 1982-1994.
McDannold et al., "Magnetic Resonance Acoustic Radiation Force Imaging", Med. Phys. vol. 35, No. 8, Aug. 2008, pp. 3748-3758.
McDannold et al., "MRI Evaluation of Thermal Ablation of Tumors with Focused Ultrasound", Journal of Magnetic Resonance Imaging, vol. 8, No. 1, Jan./Feb. 1998, pp. 91-100.
McDannold et al., "Quality Assurance and System Stability of a Clinical MRI-Guided Focused Ultrasound System: Four-Year Experience", Medical Physics, vol. 33, No. 11, Nov. 2006, pp. 4307-4313.
McGough et al., "Direct Computation of Ultrasound Phased-Array Driving Signals from a Specified Temperature Distribution for Hyperthermia", IEEE Transactions on Biomedical Engineering, vol. 39, No. 8, Aug. 1992, pp. 825-835.
Medel et al., "Sonothrombolysis: An Emerging Modality for the Management of Stroke", Neurosurgery, vol. 65, No. 5, Nov. 2009, pp. 979-993.
Mougenot et al., "MR Monitoring of the Near-Field HIFU Heating", 8th International Symposium on Therapeutic Ultrasound, AIP Conference Proceedings, vol. 1113, 2009, pp. 159-161.
Sebok et al., "Interleaved Magnetic Resonance and Ultrasound by Electronic Synchronization", Investigative Radiology, vol. 26, No. 4, 1991, pp. 353-357.

(56) References Cited

OTHER PUBLICATIONS

Shakespeare et al., "A Method for Foetal Heart Monitoring During Magneti Resonance Imaging Using Doppler Ultrasound", IOP Publishing, UK, vol. 20, No. 4, 1999, pp. 363-368.
Soher et al., "Correcting for BO Field Drill in MR Temperature Mapping with Oil References", Proc. Intl. Soc. Mag. Reson. Med., vol. 16, 2008, p. 3029.
Vimeux et al., "Real-Time Control of Focused Ultrasound Heating Based on Rapid MR Thermometry", Invest. Radiol., vol. 34, No. 3, Mar. 1999, pp. 190-193.
Vitek, Office Action, U.S. Appl. No. 13/222,086, Dec. 21, 2012, 14 pgs.
Vitek, Final Office Action, U.S. Appl. No. 13/222,086, Dec. 17, 2013, 17 pgs.
Vitek, Office Action, U.S. Appl. No. 13/222,086, May 8, 2014, 14 pgs.
Vitek, Final Office Action, U.S. Appl. No. 13/222,086, Sep. 5, 2014, 15 pgs.
Vitek, Office Action, U.S. Appl. No. 13/222,086, Aug. 21, 2015, 21 pgs.
Vitek, Office Action, U.S. Appl. No. 15/979,602, Jun. 26, 2020, 10 pgs.
Vitek, Office Action, U.S. Appl. No. 15/979,602, Dec. 24, 2020, 16 pgs.
Vykhodtseva et al., "MRI Detection of the Thermal Effects of Focused Ultrasound on the Brain", Ultrasound in Medicine & Biology, vol. 26, No. 5, Jun. 2000, pp. 871-880.

\* cited by examiner

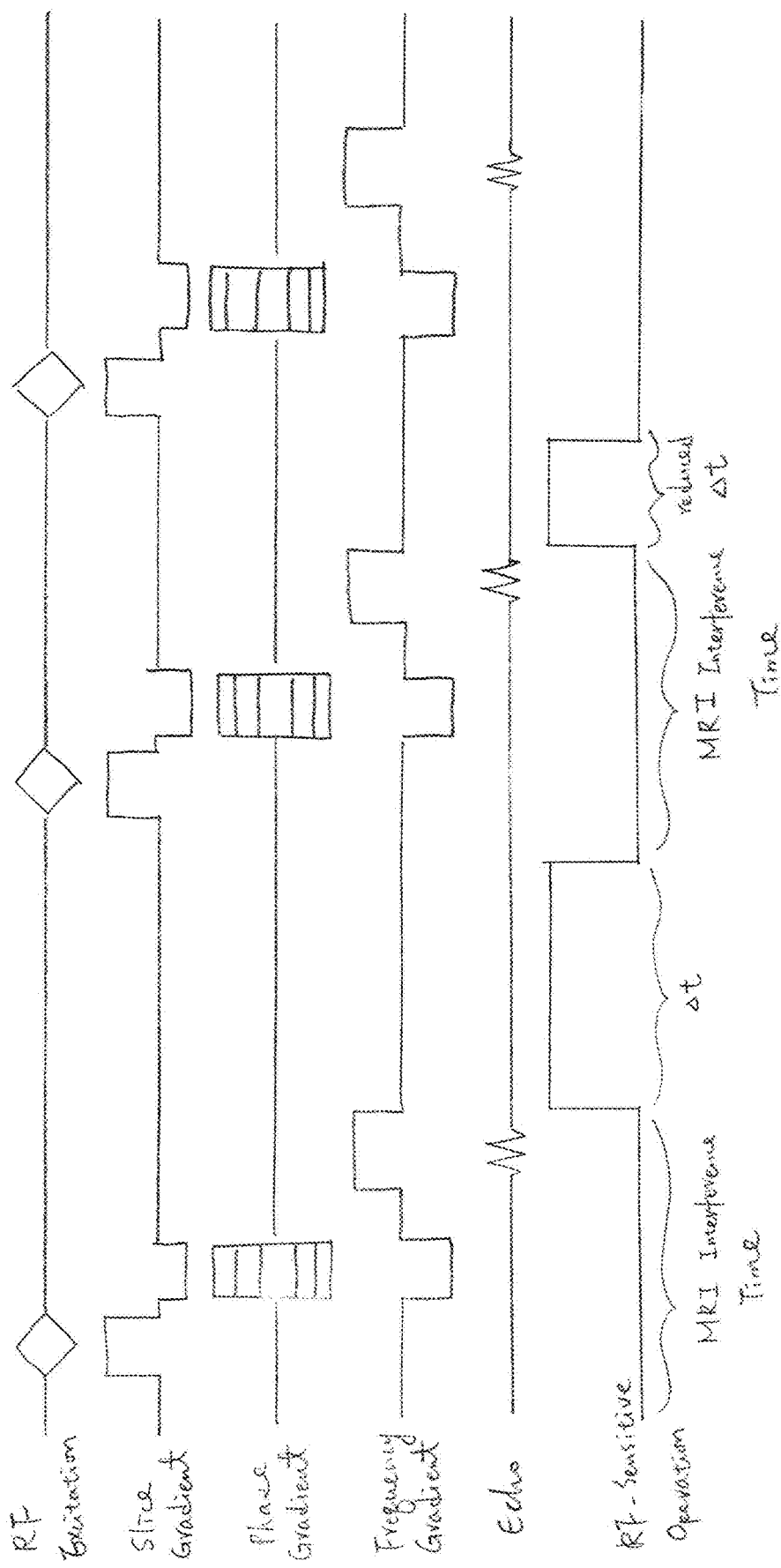

AVOIDING MRI-INTERFERENCE WITH CO-EXISTING SYSTEMS

CROSS-REFERENCE TO RELATED APPLICATION

This application is a continuation-in-part of U.S. patent application Ser. No. 15/979,602, filed on May 15, 2018, which is continuation of U.S. patent application Ser. No. 13/222,086, filed on Aug. 31, 2011. The entire disclosure of each of these applications is hereby incorporated by reference in its entirety and for all purposes.

FIELD OF THE INVENTION

The present invention relates, generally, to medical diagnosis and treatment methods guided by magnetic resonance imaging (MRI), and, more specifically, to approaches to minimizing MRI-induced interferences.

BACKGROUND

Magnetic resonance imaging may be used in conjunction with ultrasound focusing in a variety of medical applications. Ultrasound penetrates well through soft tissues and, due to its short wavelengths, can be focused to spots with dimensions of a few millimeters. As a consequence of these properties, ultrasound can be and has been used for various diagnostic and therapeutic medical purposes, including ultrasound imaging and non-invasive surgery. For example, focused ultrasound may be used to ablate diseased (e.g., cancerous) tissue without causing significant damage to surrounding healthy tissue. An ultrasound focusing system generally utilizes an acoustic transducer surface, or an array of transducer surfaces, to generate an ultrasound beam. In transducer arrays, the individual surfaces, or "elements," are typically individually controllable, i.e., their vibration phases and/or amplitudes can be set independently of one another, allowing the beam to be steered in a desired direction and focused at a desired distance. The ultrasound system often also includes receiving elements, integrated into the transducer array or provided in form of a separate detector, that help monitor the focused ultrasound treatment, primarily for safety purposes. For example, the receiving elements may serve to detect ultrasound reflected off interfaces between the transducer and the target tissue, which may result from air bubbles on the skin that need to be removed to avoid skin burns. The receiving elements may also be used to detect cavitation in overheated tissues (i.e., the formation of cavities due to the collapse of bubbles formed in the liquid of the tissue).

To visualize the target tissue and guide the ultrasound focus during therapy, magnetic resonance imaging may be used. In brief, MRI involves placing a subject, such as the patient, into a homogeneous static magnetic field, thus aligning the spins of hydrogen nuclei in the tissue. Then, by applying a radio-frequency (RF) electromagnetic pulse of the right frequency (the "resonance frequency"), the spins may be flipped, temporarily destroying the alignment and inducing a response signal. Different tissues produce different response signals, resulting in a contrast among theses tissues in MR images. Because the resonance frequency and the frequency of the response signal depend on the magnetic field strength, the origin and frequency of the response signal can be controlled by superposing magnetic gradient fields onto the homogeneous field to render the field strength dependent on position. By using time-variable gradient fields, MRI "scans" of the tissue can be obtained. Many MRI protocols utilize time-dependent gradients in two or three mutually perpendicular directions. The relative strengths and timing of the gradient fields and RF pulses are specified in a pulse sequence and may illustrated in a pulse sequence diagram.

Time-dependent magnetic field gradients may be exploited, in combination with the tissue dependence of the MRI response signal, to visualize, for example, a brain tumor, and determine its location relative to the patient's skull. An ultrasound transducer system, such as an array of transducers attached to a housing, may then be placed on the patient's head. The ultrasound transducer may include MR tracking coils or other markers that enable determining its position and orientation relative to the target tissue in the MR image. Based on computations of the required transducer element phases and amplitudes, the transducer array is then driven so as to focus ultrasound into the tumor. Alternatively or additionally, the ultrasound focus itself may be visualized, using a technique such as thermal MRI or acoustic resonance force imaging (ARFI), and such measurement of the focus location may be used to adjust the focus position. These methods are generally referred to as magnetic-resonance-guided focusing of ultrasound (MRgFUS).

The simultaneous operation of ultrasound and MRI apparatus can lead to undesired interferences. For example, MRI is very sensitive to radio-frequency (RF) noise generated by the focused ultrasound system (see, e.g., U.S. Pat. No. 6,735,461). Conversely, focused ultrasound procedures often involve RF-sensitive operations (such as the ultrasound detection that may accompany treatment with focused ultrasound) that are easily disturbed by RF excitation signals and/or time-varying field gradient generated by the MRI system. Prior-art approaches to avoiding such interference include shielding as well as signal filtering and/or processing. Shielding the ultrasound system from interfering MR signals typically requires covering or surrounding the whole transducer and associated cables in metallic shield. In some systems, however, acoustic constraints prevent complete encapsulation of the ultrasound-receiving elements, resulting in penetration of, e.g., the front layer of a receiver and/or the cables by some amount of RF noise. Filtering unwanted RF disturbances from desired RF signals requires sophisticated electronics that is often difficult to implement and might damage the wanted signal. Digital signal processing usually increases the system complexity significantly, and is sometimes insufficient to eliminate all interferences. Accordingly, there is a need for alternative approaches in MRgFUS applications to minimize or avoid interferences between the two systems.

SUMMARY

Embodiments of the present invention reduce or eliminate MRI interference with a co-existing system by exploiting MRI pulse sequences (also called "MRI recipes") that include periods when the MRI gradients are relatively inactive (or "quiet"). The co-existing system may be a treatment system such as, for example, an ultrasound imaging probe or phased-array ultrasound transducer system. The operating procedure of the co-existing system may be synchronized with the MRI recipe such that RF-sensitive operations are carried out only during time intervals when the MRI gradients are inactive (and which are typically also free of MR excitation or response signals). Inactive gradients include gradients that are substantially zero, and may further include non-zero, but temporarily constant (or "static") gradients. In practice, gradients are characterized as inactive if the RF noise that they generate is below a predetermined maximum acceptable noise limit, which generally depends on the particular application.

Avoidance of MRI-caused interference with ultrasound operations in accordance herewith is advantageous in that it generally eliminates (or at least reduces) the need for shielding, filtering, or digital signal processing of RF signals. Various embodiments of the present invention avoid the drawbacks of the prior art by confining the RF-receiving periods of the ultrasound system to time intervals in which there is no interference from MRI that would have to be shielded, filtered, or removed by post-processing. As a result, however, the total imaging or treatment time may be slightly increased. Therefore, it may be desirable for certain applications to combine the synchronization of RF-sensitive ultrasound operations and MRI gradient idle times with shielding, filtering, and/or signal processing to optimize the overall effectiveness of the MRgFUS system.

In a first aspect, the invention provides a method of performing treatment of an anatomic region in conjunction with MR imaging of the region, where the treatment includes at least one RF-sensitive operation. The RF-sensitive operation may be, for example, an ultrasound operation, which may include or consist of a cavitation or acoustic-reflection measurement or ultrasound imaging. The method involves temporarily suppressing gradient field activity during an MR imaging operation, and carrying out the RF-sensitive operation only when the gradient field activity is suppressed. Non-RF-sensitive treatment operations may be carried out while the gradient fields are active. In one implementation, a signal indicative of gradient-field-activity suppression is transmitted from an MR imaging apparatus performing the MR imaging operation to an RF device performing the RF-sensitive operation; the RF-sensitive operation is initiated in response to the signal.

In some embodiments, gradient-field-activity suppression corresponds to substantially constant gradient fields, i.e., gradient fields whose magnitude changes by less than a predetermined fraction or absolute value. For example, in certain embodiments, gradient fields are deemed "substantially constant" if their magnitude changes, at a given point in time, by less than 0.1% of their maximum change rate.

The method may further include signaling onset of the gradient-field-activity suppression by an MRI apparatus (e.g., to an apparatus performing the treatment). In some embodiments, the MR imaging conforms to a pulse sequence that specifies the onset time of the gradient-field-activity suppression; the RF-sensitive operation may begin based on this onset time. During the pulse sequence, the gradient field activity may be suppressed periodically. The pulse sequence may have an associated repetition time period. The method may include determining the end of such repetition time period, carrying out the RF-sensitive operation after the repetition time period has ended, and triggering a new repetition time period after completion of the RF-sensitive operation. In some embodiments, the method includes synchronizing the treatment and the MR imaging with a synchronization signal. Alternatively or additionally, the treatment and the MR imaging may be synchronized to a common clock. In various embodiments, the method further includes adjusting the MRI pulse sequence that includes time intervals where the gradient field activity is suppressed based at least in part on information acquired during at least one of the MRI imaging or the RF-sensitive operation. For example, the information may include the temperature increase at the anatomic region, signal quality (e.g., SNR) of acoustic reflections from the anatomic region and/or movement degree of the anatomic region. The signal indicative of the gradient-field-activity suppression may then be based on the adjusted MRI pulse sequence.

In another aspect, the invention provides a system for performing treatment of an anatomic region in conjunction with MR imaging of the region, where the treatment includes at least one RF-sensitive operation. The system includes an MRI apparatus for imaging the anatomic region (which involves gradient field activity), and a treatment controller (e.g., a controller associated with or part of the treatment system) in communication with the MRI apparatus. The treatment controller causes the RF-sensitive operation to be carried out only when the gradient field activity is suppressed. In one implementation, a signal indicative of gradient-field-activity suppression is transmitted from an MRI controller to the treatment controller, which then initiates the RF-sensitive operation in response to the signal. The system may further include an MRI controller for operating the MRI apparatus in accordance with a pulse sequence. In some embodiments, the MRI controller signals time intervals of the pulse sequence where the gradient field activity is suppressed to the treatment controller, such that the RF-sensitive operation is only performed during these time intervals. In some embodiments, the treatment controller causes performance of the RF-sensitive operation when the pulse sequence ends, and triggers repetition of the pulse sequence after completion of the RF-sensitive operation. The system may further include the treatment apparatus (which may be, e.g., an ultrasound transducer, a cavitation detection device, and/or a reflection detection device) that is in communication with the treatment controller for performing the RF-sensitive operation.

In various embodiments, the system may further include an MRI controller; the treatment controller and/or the MRI controller is configured to adjust the MRI pulse sequence that includes time intervals where the gradient-field activity is suppressed based at least in part on information acquired using the MRI apparatus and/or the treatment apparatus. For example, the information may include the temperature increase at the anatomic region, signal quality (e.g., SNR) of acoustic reflections from the anatomic region and/or movement degree of the anatomic region. In addition, the MRI controller may be further configured to operate the MRI apparatus in accordance with the adjusted MRI pulse sequence and the signal indicative of the gradient-field-activity suppression may be based on the adjusted MRI pulse sequence. In one embodiment, the system further includes a measurement system for measuring RF signals originating from the MRI apparatus; the controller is further configured to perform the RF-sensitive operation based on the measured RF signals. In addition, the treatment controller may be further configured to cause the gradient field activity to be periodically temporarily suppressed. In various embodiments, the system includes a system clock for synchronizing the RF-sensitive operation and MR imaging of the anatomic region.

In yet another aspect, a controller for synchronizing an MRI apparatus with a treatment system (such as an ultrasound system) is provided. The controller includes a first module for receiving information about an MRI pulse sequence specifying time intervals wherein gradient fields are suppressed, and a second module for initiating the RF-sensitive ultrasound operation at the onset of the gradient-field suppression based on the information.

A further aspect of the invention is directed to an MRI system operable in conjunction with a treatment system for performing MR imaging of an anatomic region in conjunction with treatment of the region (which includes one or more RF-sensitive operations). The MRI system includes an MRI apparatus for imaging the anatomic region and an MRI controller. The MRI controller operates the MRI apparatus in accordance with a pulse sequence that includes time intervals of gradient field activity as well as time intervals where the gradient field activity is suppressed. The controller signals the time intervals where the gradient field activity is suppressed to the treatment apparatus so as to cause performance of the RF-sensitive operation during these time intervals.

Another aspect is directed to a treatment system operable in conjunction with an MRI system for performing treatment (including RF-sensitive operations) of an anatomic region in conjunction with MR imaging of the region. The system includes a treatment apparatus (such as, or including, an ultrasound transducer) for performing the treatment, and treatment controller for causing performance of the RF-sensitive operation in response to an end of an MRI pulse sequence comprising gradient field activity, and triggering repetition of the pulse sequence after completion of the RF-sensitive operation.

As used herein, the term "substantially" means±10%, and in some embodiments, ±5%. "Clinically intolerable" means having an undesired (and sometimes the lack of a desired) effect on tissue that is considered significant by clinicians, e.g., the onset of damage thereto. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing will be more readily understood from the following detailed description, in particular, when taken in conjunction with the drawings, in which:

FIGS. 6A-6C are pulse sequence diagrams illustrating various exemplary MRI protocols as well as synchronization-signal and ultrasound-detection periods in accordance with various embodiments.

DETAILED DESCRIPTION

Figure 1:
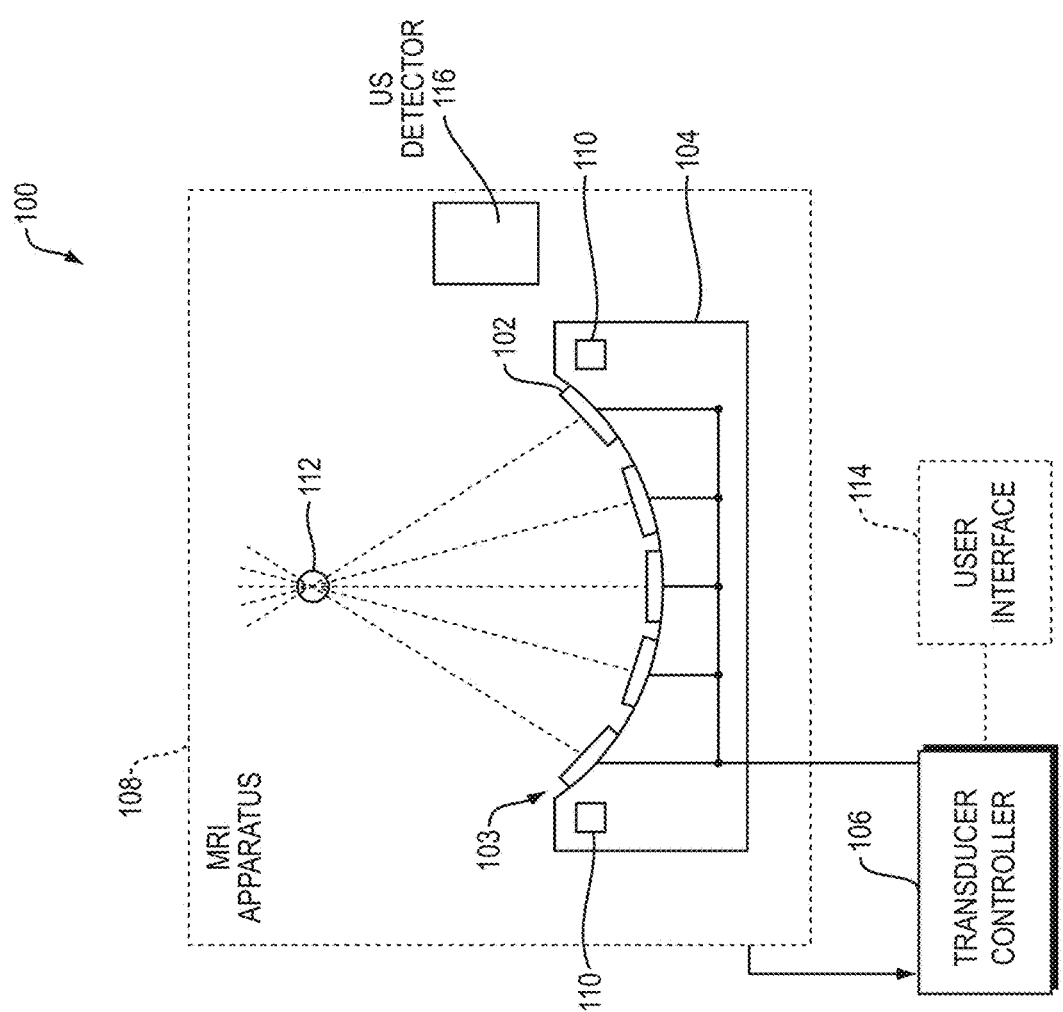
FIG. 1 is a schematic drawing of an MRgFUS system in accordance with one embodiment.
Figure 2:
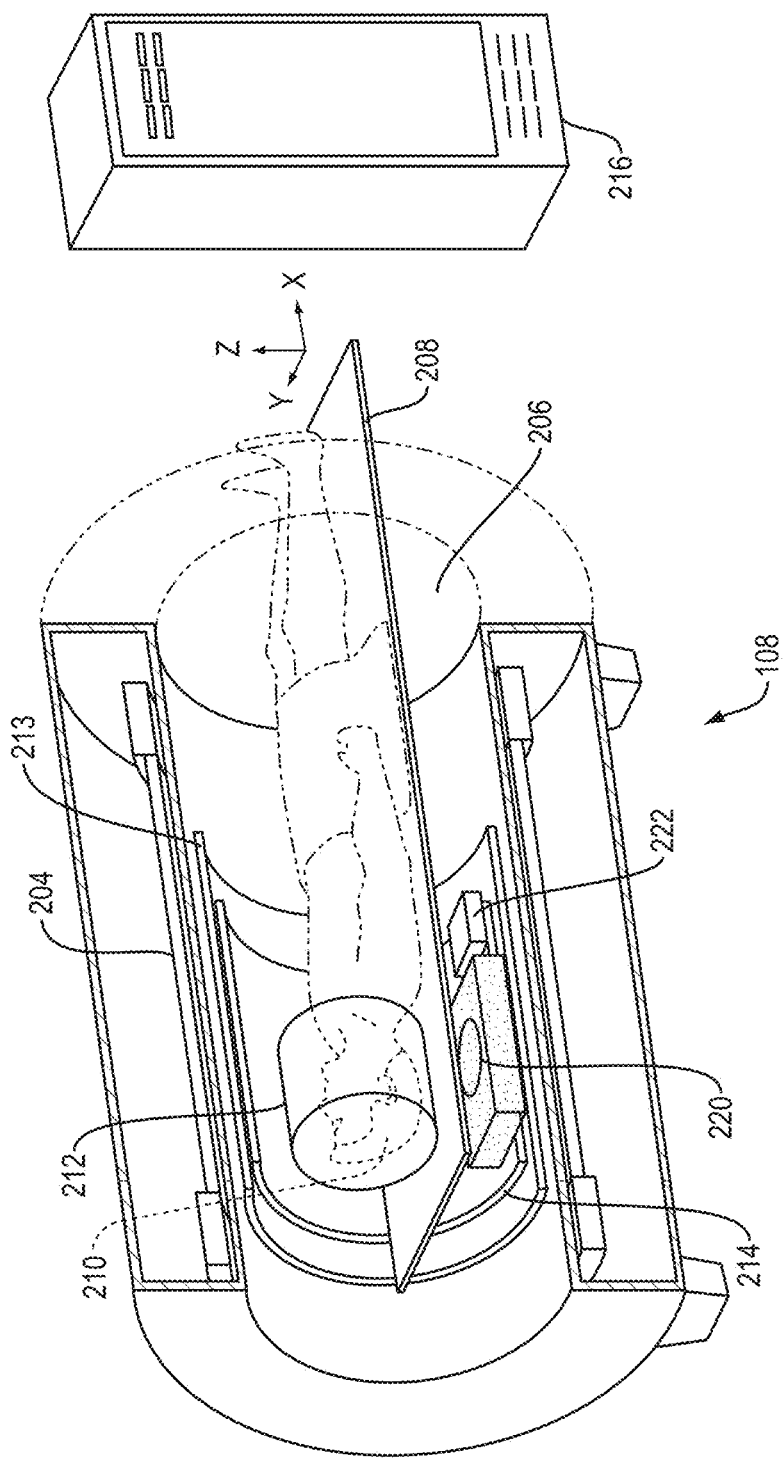
FIG. 2 is a perspective view of an MRgFUS system in accordance with one embodiment.

FIGS. 1 and 2 illustrate an exemplary MRgFUS system 100 in which synchronization of ultrasound and MRI procedures may advantageously be practiced. As shown in FIG. 1, the system 100 includes a plurality of ultrasound transducer elements 102, which are arranged in an array 103 at the surface of a housing 104. The array may comprise a single row or a matrix of transducer elements 102. In alternative embodiments, the transducer elements 102 may be arranged without coordination, i.e., they need not be spaced regularly or arranged in a regular pattern. The array may have a curved (e.g., spherical or parabolic) shape, as illustrated, or may include one or more planar or otherwise shaped sections. Its dimensions may vary, depending on the application, between millimeters and tens of centimeters. The transducer elements 102 may be piezoelectric ceramic elements. Piezo-composite materials, or generally any materials capable of converting electrical energy to acoustic energy, may also be used. To damp the mechanical coupling between the elements 102, they may be mounted on the housing using silicone rubber or any other suitable damping material.

The transducer elements 102 are separately controllable, i.e., they are each capable of emitting ultrasound waves at amplitudes and/or phases that are independent of the amplitudes and/or phases of the other transducers. A transducer controller 106 serves to drive the transducer elements 102. For n transducer elements, the controller 106 may contain n control circuits each comprising an amplifier and a phase delay circuit, each control circuit driving one of the transducer elements. The controller 106 may split an RF input signal, typically in the range from 0.1 MHz to 4 MHz, into n channels for the n control circuit. It may be configured to drive the individual transducer elements 102 of the array at the same frequency, but at different phases and different amplitudes so that they collectively produce a focused ultrasound beam. The transducer controller 106 desirably provides computational functionality, which may be implemented in software, hardware, firmware, hardwiring, or any combination thereof, to compute the required phases and amplitudes for a desired focus location. In general, the controller 106 may include several separable apparatus, such as a frequency generator, a beamformer containing the amplifier and phase delay circuitry, and a computer (e.g., a general-purpose computer) performing the computations and communicating the phases and amplitudes for the individual transducer elements 102 to the beamformer. Such systems are readily available or can be implemented without undue experimentation.

The system 100 further includes an MRI apparatus 108 for imaging the target tissue and/or ultrasound focus. To aid in determining the relative position of transducer array and MRI apparatus 108, the transducer array may have MR trackers 110 associated with it, arranged at a fixed position and orientation relative to the array. The trackers 110 may, for example, be incorporated into or attached to the housing 104. If the relative positions and orientations of the MR trackers 110 and transducers 102 are known, MR scans of the MR trackers 110 implicitly reveal the transducer location in MRI coordinates, i.e., in the coordinate system of the MRI apparatus 108. The transducer controller 106, which receives MRI data containing the MR tracker location, can then set the phases and amplitudes of the transducers 102 to generate a focus 112 at a desired location or within a desired target region. In some embodiments, a user interface 114 in communication with the transducer controller 106 and/or the MRI apparatus 108 facilitates the selection of the focus location or region in MR coordinates.

The system 100 generally also has the capability to detect ultrasound, which serves to monitor the application of ultrasound for safety purposes. For example, ultrasound reflections off tissue interfaces that intersect the ultrasound beam path may be analyzed to ensure, if necessary by adjustment of the treatment protocol, that such interfaces are not inadvertently overheated. Further, measurements of the received cavitation spectrum may be used to detect cavitation resulting from the interaction of ultrasound energy with water-containing tissue. In addition, the visualization of the tissue and target may be supplemented by ultrasound imaging, for example, to facilitate tracking a moving target. Ultrasound detection may be accomplished with the ultrasound transducer array 103. For example, treatment and imaging periods may be interleaved, or a contiguous portion of the array 103 or discontiguous subset of transducer elements 102 may be dedicated to imaging while the remainder of the array 103 focuses ultrasound for treatment purposes. Alternatively, a separate ultrasound receiver 116, which may be, e.g., a simple ultrasound probe or array of elements or a hydrophone, may be provided. The separate receiver 116 may be placed in the vicinity of the ultrasound transducer array 103, or even integrated into its housing 104. If synchronization in accordance herewith is not utilized, the ultrasound receiver 116 needs to be shielded, e.g., by a surrounding conductive structure serving as a Faraday cage, to be at least partially effective.

FIG. 2 illustrates the MRI apparatus 108 in more detail. The apparatus 108 may include a cylindrical electromagnet 204, which generates the requisite static magnetic field within a bore 206 of the electromagnet 204. During medical procedures, a patient is placed inside the bore 206 on a movable support table 208. A region of interest 210 within the patient (e.g., the patient's head) may be positioned within an imaging region 212 wherein the electromagnet 204 generates a substantially homogeneous field. A set of cylindrical magnet field gradient coils 213 may also be provided within the bore 206 and surrounding the patient. The gradient coils 213 generate magnetic field gradients of predetermined magnitudes, at predetermined times, and in three mutually orthogonal directions. With the field gradients, different spatial locations can be associated with different precession frequencies, thereby giving an MR image its spatial resolution. An RF transmitter coil 214 surrounding the imaging region 212 emits RF pulses into the imaging region 212, and receives MR response signals emitted from the region of interest 210. (Alternatively, separate MR transmitter and receiver coils may be used.)

The MRI apparatus 108 generally includes an MRI controller 216 that controls the pulse sequence, i.e., the relative timing and strengths of the magnetic field gradients and the RF excitation pulses and response detection periods. The MRI controller 216 may be combined with the transducer controller 106 into an integrated system control facility. The MR response signals are amplified, conditioned, and digitized into raw data using an image processing system, and further transformed into arrays of image data by methods known to those of ordinary skill in the art. Based on the image data, a treatment region (e.g., a tumor) is identified. The image processing system may be part of the MRI controller 216, or may be a separate device (e.g., a general-purpose computer containing image processing software) in communication with the MRI controller 216 and/or the transducer controller 106. An ultrasound phased array 220, disposed within the bore 206 of the MRI apparatus and, in some embodiments, within the imaging region 212, is then driven so as to focus ultrasound into the treatment region. The drive signals are based on the MRI images, which provide information about the position and orientation of the transducer surface(s) with respect to the MRI apparatus and/or the focus location. To monitor the ultrasound treatment, an ultrasound receiver 222 may also be disposed within the bore 206 of the MRI apparatus.

In some embodiments, MR imaging is simultaneously used to quantitatively monitor in vivo temperatures. This is particularly useful in MRgFUS treatment, where the temperature of the treatment target is preferred to be continuously monitored in order to assess the progress of treatment and correct for local differences in heat conduction and energy absorption to avoid damage to non-target tissues surrounding the target. The monitoring (e.g., measurement and/or mapping) of temperature with MR imaging is generally referred to as MR thermometry or MR thermal imaging.

Among various methods available for MR thermometry, the proton resonance frequency (PRF) shift method is often the method of choice due to its excellent linearity with respect to temperature change, near-independence from tissue type, and temperature map acquisition with high spatial and temporal resolution. The PRF shift method is based on the phenomenon that the MR resonance frequency of protons in water molecules changes linearly with temperature (with a constant of proportionality that, advantageously, is relatively constant between tissue types). Since the frequency change with temperature is small, only −0.01 ppm/° C. for bulk water and approximately −0.0096 to −0.013 ppm/° C. in tissue, the PRF shift is typically detected with a phase-sensitive imaging method in which the imaging is performed twice: first to acquire a baseline PRF phase image prior to a temperature change and then to acquire a second phase image after the temperature change—i.e., a treatment image—thereby capturing a small phase change that is proportional to the change in temperature. A map of temperature changes may then be computed from the (reconstructed, i.e., real-space) images by determining, on a pixel-by-pixel basis, phase differences between the baseline image and the treatment image, and converting the phase differences into temperature differences based on the PRF temperature dependence while taking into account imaging parameters such as the strength of the static magnetic field and echo time (TE) (e.g., of a gradient-recalled echo).

If the temperature distribution in the imaged area at the time of acquisition of the baseline image is known, the temperature-difference map can be added to that baseline temperature in order to obtain the absolute temperature distribution corresponding to the treatment image. In some embodiments, the baseline temperature is simply uniform body temperature throughout the imaging region. More complicated baseline temperature distributions are, in some embodiments, determined prior to treatment by direct temperature-measurements in various locations in combination with interpolation and/or extrapolation based on a mathematical fit (e.g., a smooth, polynomial fit).

Figure 3A:
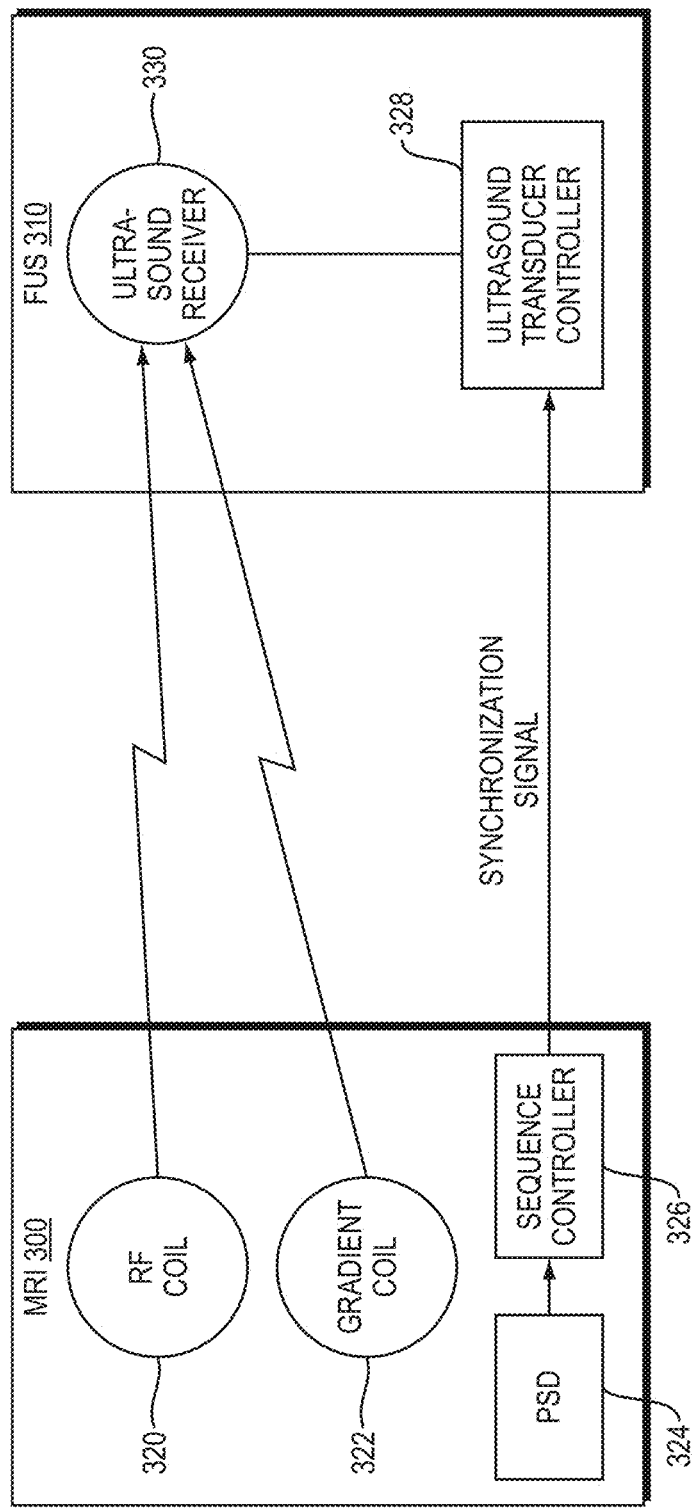
FIGS. 3A-3C are schematic drawings illustrating the interaction between an MRI apparatus and an ultrasound transducer in accordance with various embodiments.
Figure 3B:
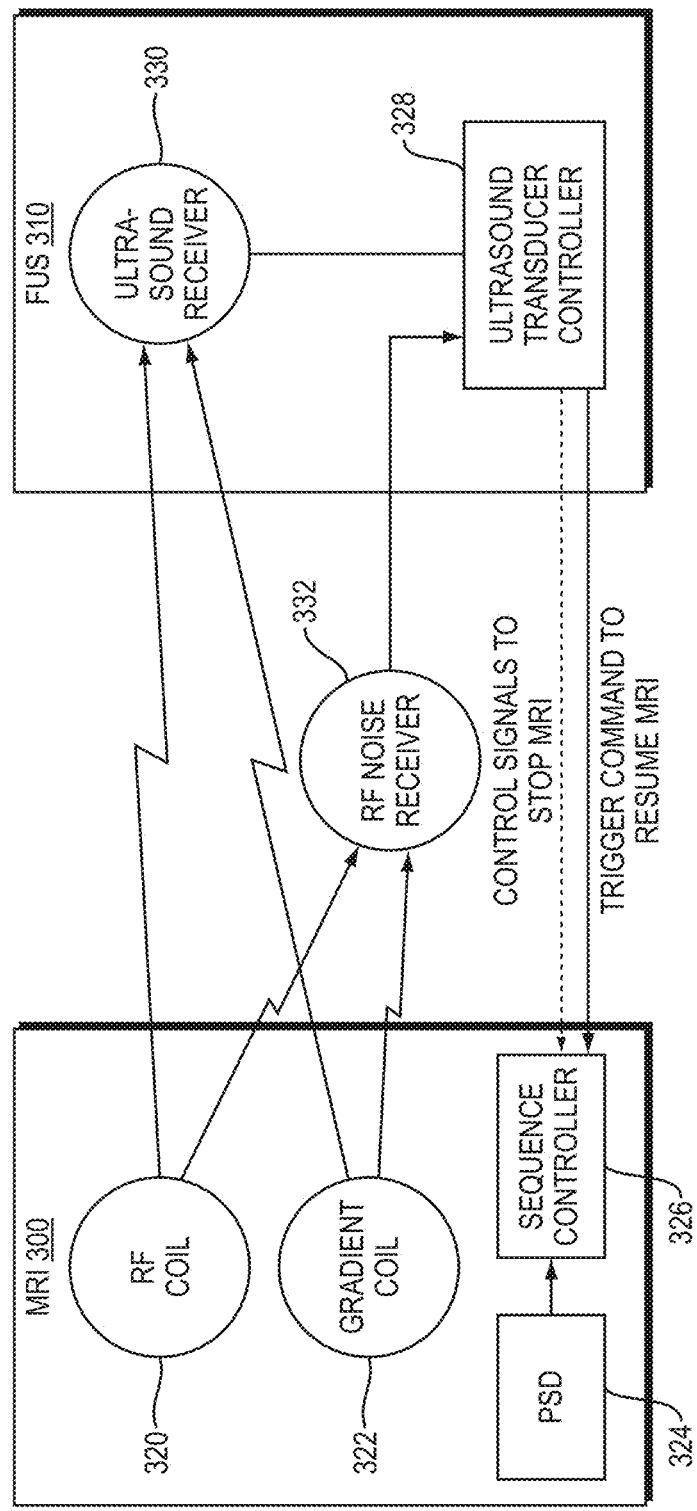
Figure 3C:
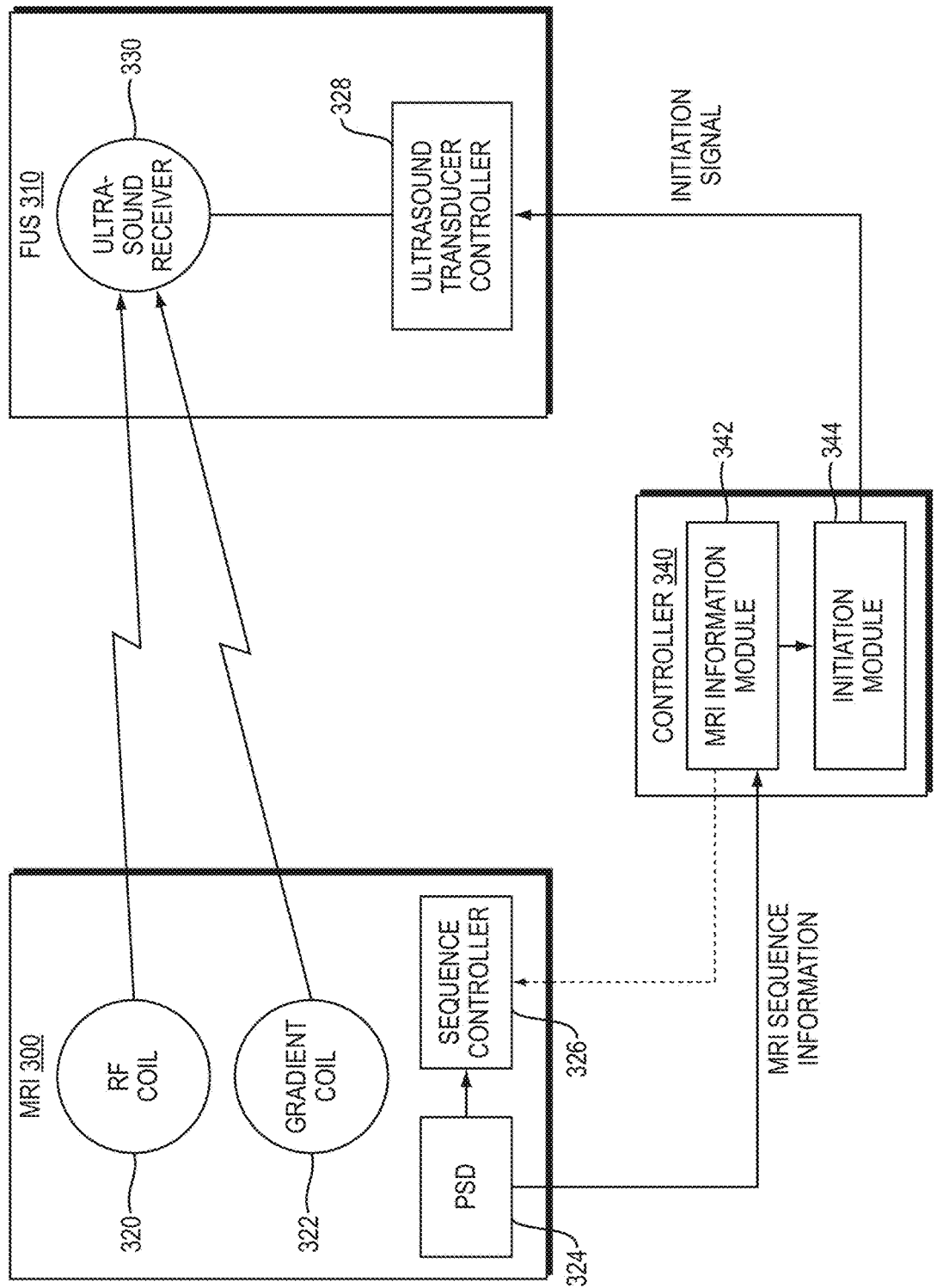

FIGS. 3A-3C schematically illustrates the interaction between an MRI apparatus 300 and a focused ultrasound system 310 in accordance with various embodiments of the invention. The MRI apparatus 300 includes RF transmitter coils 320, and gradient coils 322 for generating time-varying magnetic gradients across the tissue to be imaged. Both transmitter-coil and gradient-coil emissions fall in the RF range and can potentially disturb focused ultrasound procedures. The MRI transmitter coils 320 generate electromagnetic pulses with frequencies in the range from about 50 MHz to about 150 MHz to induce spin flipping. The gradients generated by the gradient coils 322 are typically updated at kHz or MHz frequencies, and are substantially constant between successive updates. For example, the gradient value (i.e., the magnetic field strength of the gradient field) may be controlled digitally at a sampling rate of 250 kHz by applying a new voltage every four microseconds. These small control steps generate RF noise, mainly at the sampling frequency (i.e., 250 kHz in the example) and its harmonics (i.e., 500 kHz, 750 kHz, etc.). A step in the gradient value is usually implemented by a controlled ramp whose slope is proportional to the voltage step. The resulting RF noise is generally proportional to the voltage step as well. However, even during nominally static gradients, control steps exist and resulting in some level of RF noise (although significantly less than is generated during ramps). In other words, non-zero static gradients are quieter than dynamic gradients, but are not completely quiet.

The MRI apparatus 300 includes a database 324 (stored, e.g., on a hard drive of a computer, which may be the same computer as is used for MR image processing) for storing pulse sequence diagrams (PSDs). An associated sequence controller 326 within the MRI controller 216 operates the MRI apparatus in accordance with the specified pulse sequences. As illustrated in FIG. 3A, the sequence controller 326 may provide a synchronization signal to the ultrasound control module 328, signaling the onset of gradient idle times, i.e., time intervals in which magnetic field gradients, or time variations thereof, are completely or partially suppressed. The ultrasound controller module 328 may be implemented in the transducer controller 106, and initiate RF-sensitive ultrasound operations only during the gradient idle times.

Ultrasound operations that are particularly sensitive to RF disturbances from the MRI apparatus 300 include ultrasound imaging (in parallel with MRI) and measurements of the cavitation spectrum or of acoustic reflections, all of which generally have low signal voltages associated with them (e.g., voltages in the mV range and below). During these measurements, the ultrasound receiver 330 (which may be the transducer operated in "listening" mode, or a separate, dedicated receiver device such as a hydrophone) converts the acoustic signals into electrical RF signals. Such signals can also be created by the RF disturbances from the MRI apparatus 300, resulting in unwanted signal components. Since the detected signals generally have lower power than, e.g., focused ultrasound ablation pulses, they are particularly sensitive to such perturbations.

Figure 4A:
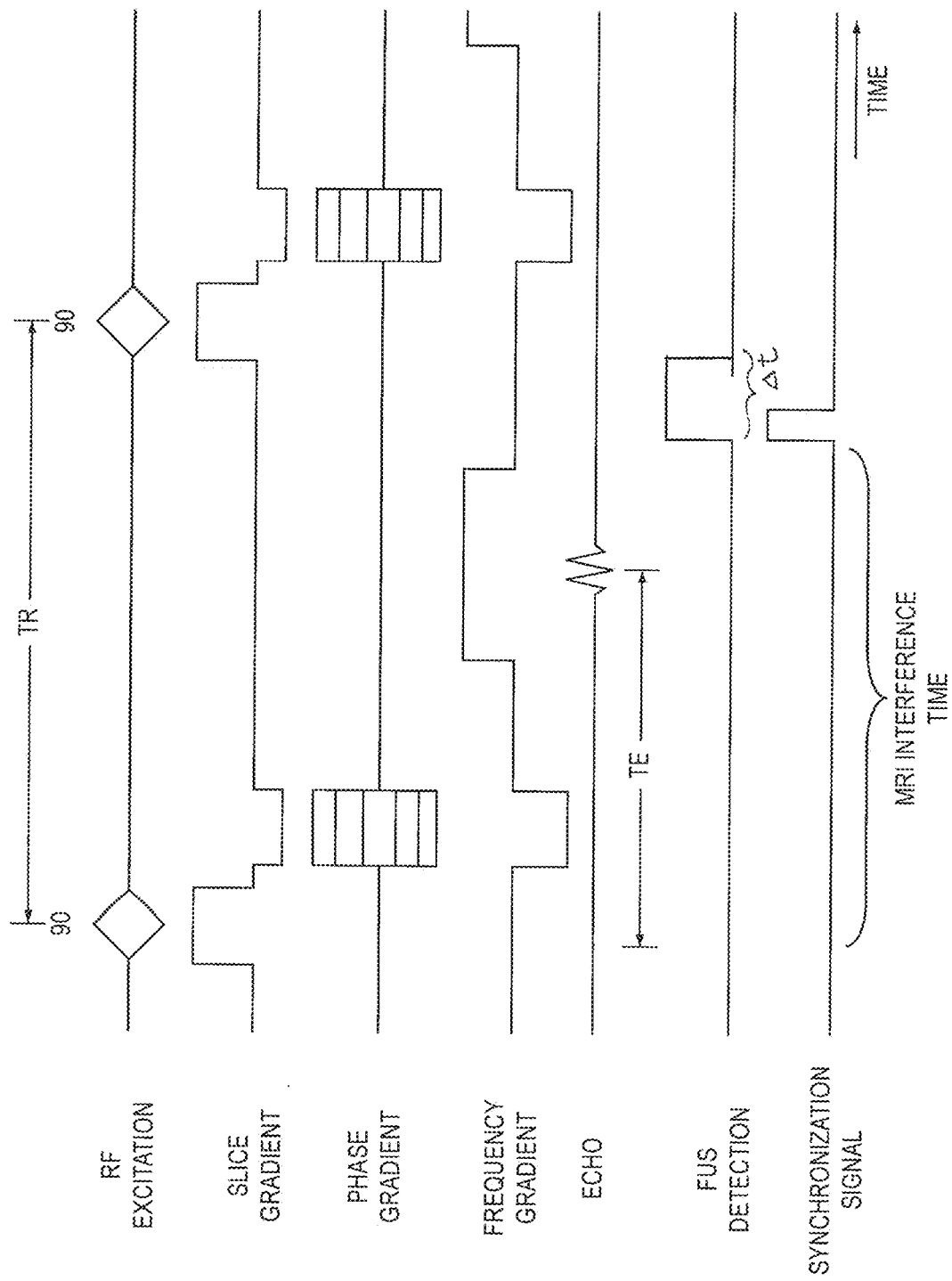
FIG. 4A is a pulse sequence diagram illustrating an exemplary MRI protocol as well as synchronization-signal and ultrasound-detection periods in accordance with one embodiment.

FIG. 4A shows a PSD illustrating, for a typical MR gradient echo pulse sequence, the relative timing of the RF excitation pulse, the magnetic field gradients in three directions, and the MR response signal, which occurs at the echo time (TE). The sequence may be periodically repeated; the period is denoted as the repetition time TR and may be, for example, in the range from 20 to 30 ms. FIG. 4A further shows the timing of the synchronization signal relative to the MRI sequence, as well as the period, Δt, during which RF-sensitive ultrasound operations (i.e., generally, ultrasound detection) may be carried out, which may last, for example, 1 ms. Ultrasound operations that are not especially sensitive to RF disturbances may be carried out at any time, including periods during which the MRI gradients are active. In fact, focused ultrasound application times are often in the range from about 10 to about 30 seconds. Thus, ultrasound application may begin long before and end long after the MRI sequence. In embodiments in which the ultrasound transducer is alternately used for focused ultrasound application and RF-sensitive ultrasound detection, the non-RF-sensitive operations (e.g., ultrasound treatment) are preferably carried out during active-gradient periods, reserving the gradient idle times for RF-sensitive operations (e.g., measurements of the reflections off tissue interfaces, measurements of the cavitation spectrum and/or ultrasound imaging).

Figure 4B:
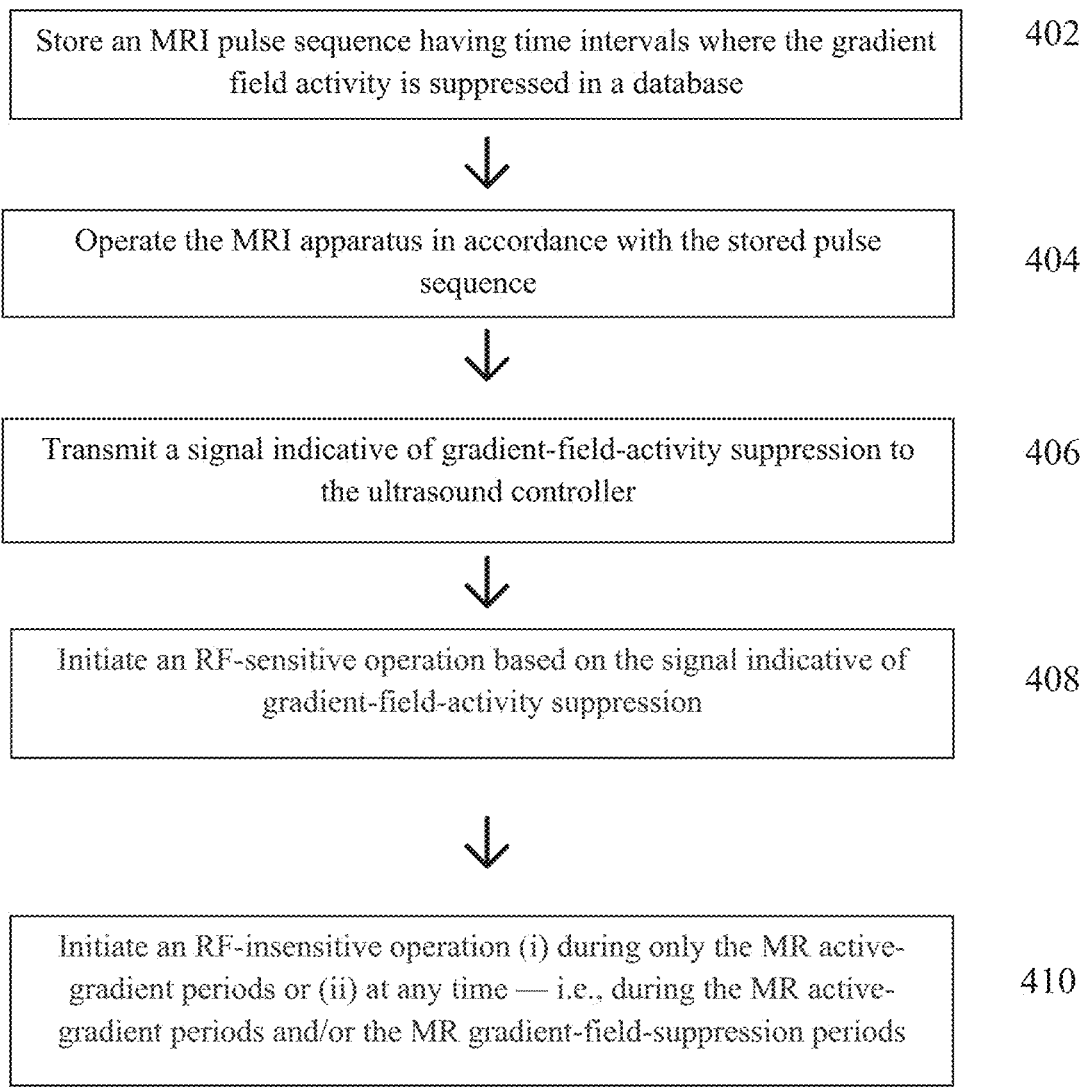
FIGS. 4B-4D are flow charts illustrating various approaches of performing MR imaging of an anatomic region in conjunction with an RF-sensitive operation in accordance with some embodiments.

In the PSD shown in FIG. 4A, gradient idle time is added to each repetition time period by design. During the idle time, the MRI apparatus 300 sends a synchronization signal to the ultrasound system 310, which then performs spectrum measurements and other RF-sensitive operations. Synchronization between MRI and ultrasound detection is, thus, internally controlled by the MRI recipe. Thus, as depicted in FIG. 4B, in various embodiments, an MRI pulse sequence having time intervals when the gradient field activity is suppressed is first stored in a database in memory (in step 402). The MRI sequence controller 326 may operate the MRI apparatus 300 in accordance with the stored pulse sequence (such as application and suppression of the gradient-field activity) (in step 404). In addition, the MRI sequence controller 326 may transmit a signal indicative of gradient-field-activity suppression to the ultrasound controller 328 (in step 406). The signal may indicate the entire time intervals, the end of the gradient-field-activity application, or the onset time of the gradient-field-activity suppression. Upon receiving the signal, the ultrasound controller 328 may initiate the RF-sensitive operation based on the signal using the approaches described above (in step 408). Additionally, the RF-insensitive ultrasound operations may be carried out (i) during only the MR active-gradient periods or (ii) at any time—i.e., during the MR active-gradient periods and/or the MR gradient-field-suppression periods (in step 410).

Figure 4C:
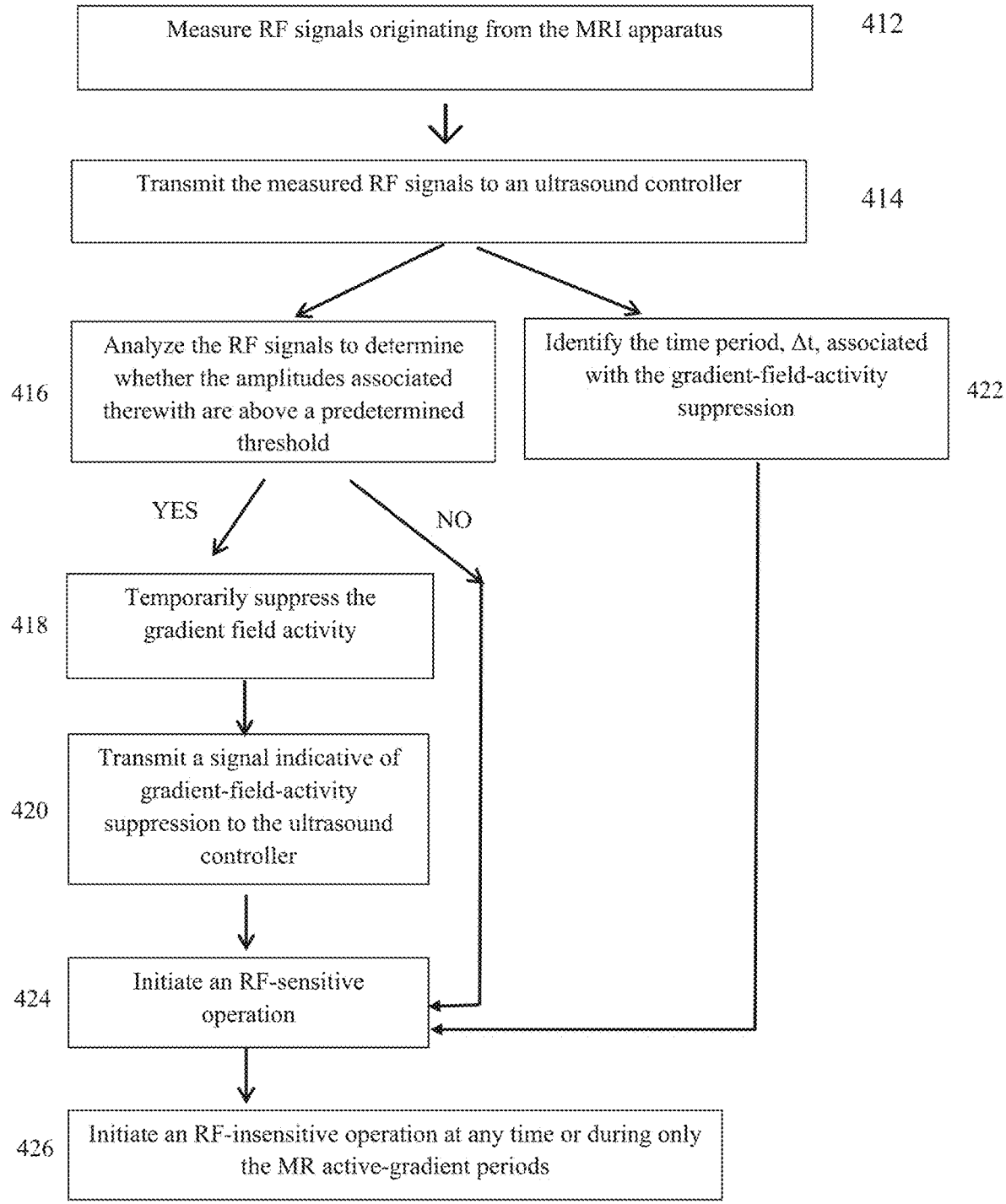

In alternative embodiments, synchronization may be effected through control mechanisms external to the MRI recipe. For example, as illustrated in FIG. 3B, the ultrasound controller module 328 may control the timing of RF-sensitive operations based on measurements of RF signals originating from the MRI apparatus 300, which may be performed, for example, by the ultrasound receiver 330 or by a separate, dedicated RF-noise receiver 332 in communication with the module 328. The MRI sequence may stop running after each repetition period (either automatically or based on an external control signal), and the focused ultrasound system may identify the end of a repetition period (e.g., by measuring RF signals generated by the MRI apparatus), perform the ultrasound measurements, and then send a trigger command to the MRI apparatus to resume the MRI sequence, i.e., proceed to the next repetition period. The MRI sequence may be interrupted after each repetition time, or after a multiple of the repetition time (such that one or more repetition periods are skipped before the next ultrasound measurement is carried out). The system may also be programmed to perform ultrasound measurements only after certain MRI procedures, for example, only after thermal imaging sequences. External control generally provides a high degree of flexibility in timing MR imaging and RF-sensitive ultrasound operations, thereby facilitating time efficiency in the overall procedure. The flow chart in FIG. 4C illustrates MR imaging of an anatomic region in conjunction with a sequence of ultrasound operations, including RF-sensitive operations and RF-insensitive operations, in accordance with some embodiments. In a first step 412, the ultrasound receiver 330 and/or separate, dedicated RF-noise receiver 332 in communication with the ultrasound controller 328 may measure RF signals originating from the MRI apparatus 300. In step 414, the ultrasound receiver 330 and/or separate RF-noise receiver 332 may transmit the measured RF signals to the ultrasound controller 328. The ultrasound controller 328 may analyze the RF signals to determine whether the amplitudes associated therewith are above a predetermined threshold (step 416). If so, the ultrasound controller 328 may transmit a signal to the MRI controller 326 to cause the gradient field activity to be temporarily suppressed (e.g., by causing the MRI sequence to stop running) (step 418). The MRI sequence controller 326 may then transmit a signal indicative of gradient-field-activity suppression to the ultrasound controller 328 (step 420). Alternatively, the ultrasound controller 328 may identify the time period, $\Delta t$, associated with the gradient-field-activity suppression (e.g., by measuring RF signals generated by the MRI apparatus) (step 422). Subsequently, the ultrasound controller 328 may initiate the RF-sensitive operation as described above (in a seventh step 424). Additionally, the RF-insensitive ultrasound operations may be carried out (i) during only the MR active-gradient periods or (ii) at any time—i.e., during the MR active-gradient periods and/or the MR gradient-field-suppression periods (in step 426).

Figure 4D:
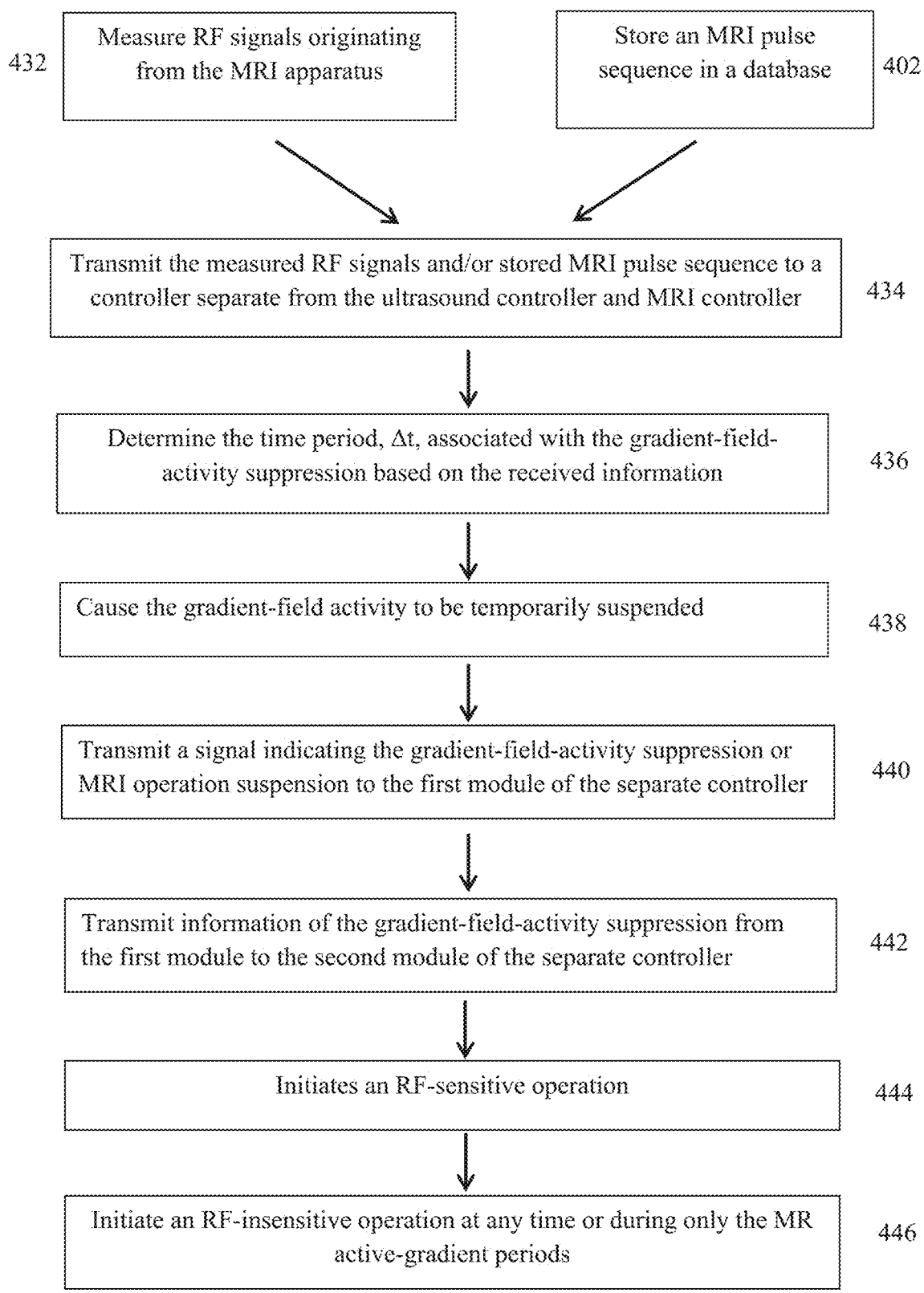

The synchronization of the MRI and focused ultrasound apparatus 300, 310 may be modified in additional ways. For example, the sequence controller 326 and ultrasound controller module 328 may be integrated into a single control module that sends synchronization or clock signals simultaneously to both apparatus 300, 310, or controls the MRI transmitter coils 320, gradient coils 322, and ultrasound receiver 330 directly. Alternatively, as shown in FIG. 3C, a separate controller 340 may communicate with conventional MRI and ultrasound apparatus that each include their individual controllers. The controller 340 may include a first module 342 that determines when gradient-field activity is suppressed, e.g., based on information it receives about an MRI pulse sequence specifying time intervals during which the gradients are quiet. The module 342 may also send control signals to the sequence controller 326 to stop MRI operation at the end of a sequence. The first module 342 may communicate gradient idle time to a second module 344 responsible for initiating the RF-sensitive treatment operation. The flow chart depicted in FIG. 4D illustrates controlling operations of MR imaging and ultrasound operations (including RF-sensitive measurements/treatments and RF-insensitive measurements/treatments) using the separate controller 340 in accordance with various embodiments. In a first step 432, the ultrasound receiver 330 and/or the separate RF-noise receiver 332 may measure the RF signals originating from the MRI apparatus 300. In step 434, the ultrasound receiver 330 and/or separate RF-noise receiver 332 may transmit the measured RF signals to the separate controller 340. Additionally or alternatively, the controller 340 may receive the information about the MRI pulse sequence from the MRI sequence controller 326. In step 436, the controller 340 may use the first module 342 to determine the time period, $\Delta t$, associated with the gradient-field-activity suppression based on the information received from the MRI sequence controller 326, the ultrasound receiver 330 and/or the separate RF-noise receiver 332. Optionally, in step 438, the controller 340 may use the second module 344 to send control signals to the MRI sequence controller 326 to temporarily suspend the gradient-field activity or stop MRI operation at the end of the current sequence. In step 440, the MRI sequence controller 326 may transmit a signal indicating the gradient-field-activity suppression or MRI operation suspension to the first module 342. In step 442, the first module may communicate the gradient-field-activity suppression to the second module 344, which then initiates the RF-sensitive operation (in a seventh step 444). Additionally, the RF-insensitive ultrasound operations may be carried out (i) during only the MR active-gradient periods or (ii) at any time—i.e., during the MR active-gradient periods and/or the MR gradient-field-suppression periods (in step 446).

In general, functionality for synchronizing an MRI apparatus and a focused ultrasound system as described above, whether integrated with the MRI controller 326 and/or ultrasound controller 328 or provided by a separate controller 340, may be structured in one or more modules implemented in hardware, software, or a combination of both. For embodiments in which the functions are provided as one or more software programs, the programs may be written in any of a number of high level languages such as FORTRAN, PASCAL, JAVA, C, C++, C#, BASIC, various scripting languages, and/or HTML. Additionally, the software can be implemented in an assembly language directed to the microprocessor resident on a target computer; for example, the software may be implemented in Intel 80x86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the first and second modules 342, 344 may be implemented in software stored in memory of a general-purpose computer (e.g., in system memory—typically random-access memory (RAM)—during use, and/or on a hard drive, CD-ROM, or other non-volatile storage medium for long-term storage), and executed by the computer's processor. The database 324 may, likewise, be stored long-term in non-volatile memory, and loaded into system memory during use. The modules 342, 344 may be programmed in any suitable programming language, including, without limitation, high-level languages such as C, C++, C#, Ada, Basic, Cobra, Fortran, Java, Lisp, Perl, Python, Ruby, or Object Pascal, or low-level assembly languages. Communications between the ultrasound system, the MRI apparatus and the separate controller 340 may be established via, e.g., Bluetooth, WLAN, an 802.11 protocol, an Ethernet network, or any other wired or wireless connection.

Figure 5A:
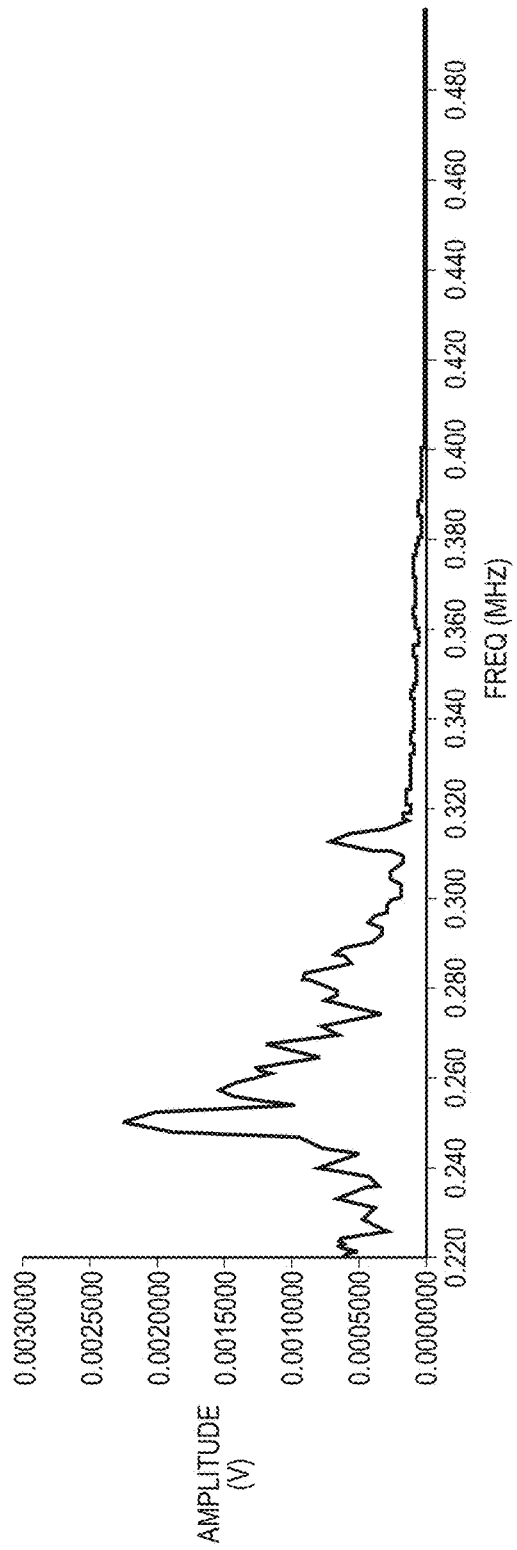
FIG. 5A is a spectrum of an MRI interference signals detected by the ultrasound receiver in the absence of synchronization.
Figure 5B:
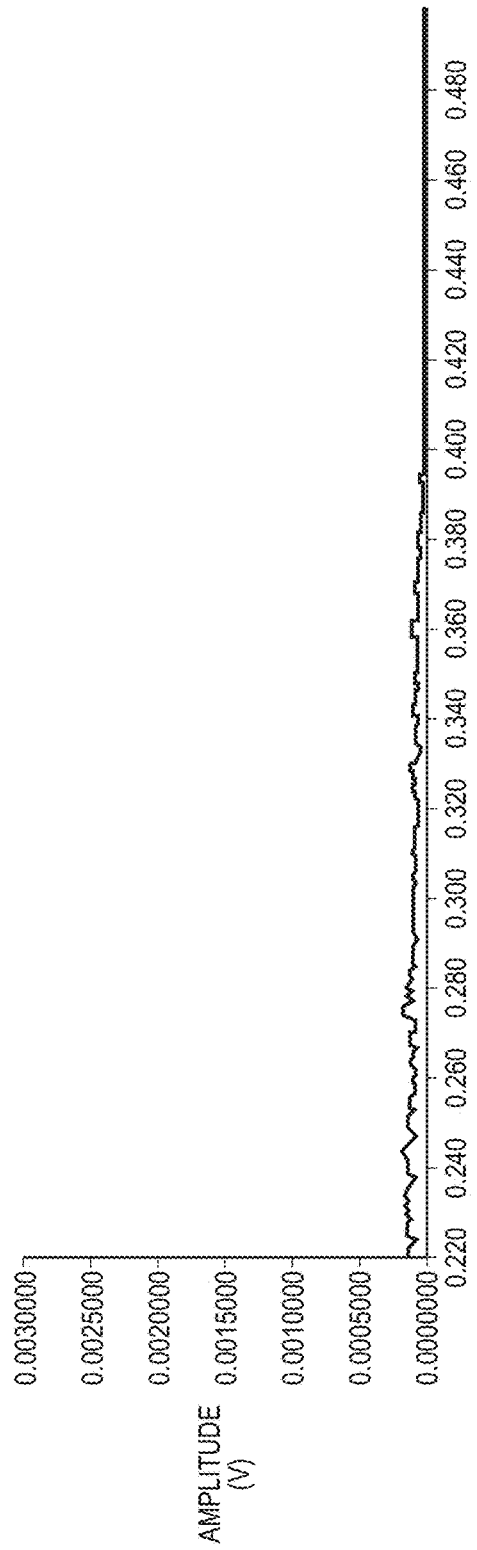
FIG. 5B is a spectrum of an MRI interference signal detected by the ultrasound receiver after synchronization in accordance with one embodiment.

FIGS. 5A and 5B show the spectra of MRI interference signals detected by the ultrasound transducer with and without synchronization of the detection period with gradient idle times. As illustrated, synchronization can reduce MRI disturbances by about an order of magnitude. Note that the signals in FIGS. 5A and 5B are free of cavitation effects.

FIG. 5A shows a signal corrupted by gradient noise, while FIG. 5B, shows a clean signal that contains only background noise.

In some embodiments, the synchronization methods described above are used in conjunction with shielding, signal filtering, and/or processing. This allows RF-sensitive operations to be carried out during portions of MR sequences in which the gradients are sufficiently inactive. For example, if synchronization is combined with shielding, there is generally a trade-off between the amount of shielding used and the maximum acceptable noise. The less shielding is used, the quieter the gradients need to be to avoid undesired interference between the MRI system and the ultrasound (or other co-existing) system. Noise reductions due to shielding depend on the particular material used (e.g., iron, copper, or nickel) as well as on the frequency range of interest, and can readily be ascertained based on graphs and tabulations of absorption and reflection coefficients that are available in the literature. For example, at frequencies of around 1 MHz, a 3 mm thick iron shield reduces the noise by about 100 dB. For a given maximum acceptable noise level (which, in turn, depends on the signal filtering and processing capabilities of the system), the maximum allowable gradients can be computed based on the noise reduction achieved by shielding.

Figure 6A:
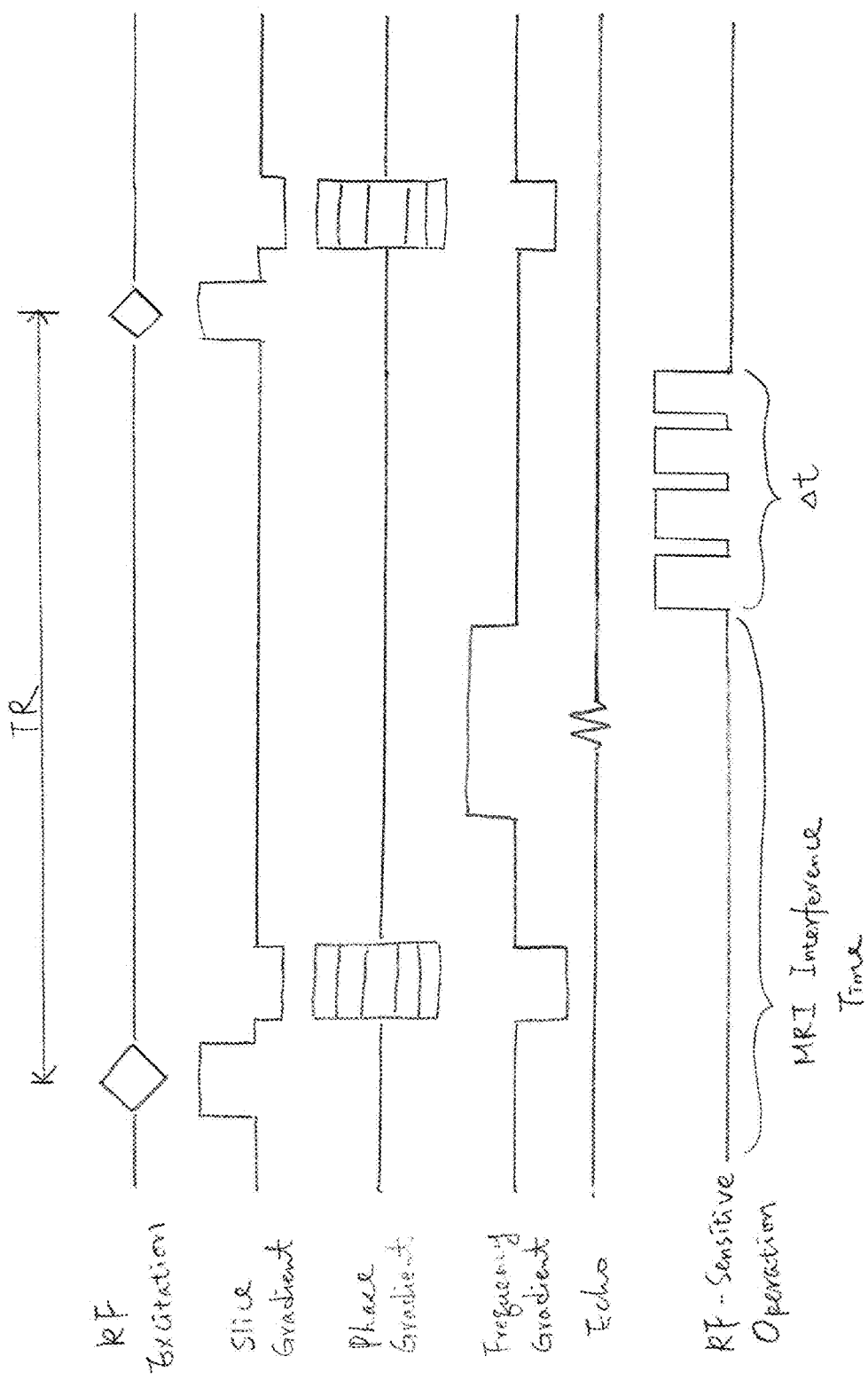

In various embodiments, the repetition period of the MRI gradient pulses in the sequence is dynamically changed based on information acquired during the MRI imaging and/or the RF-sensitive operation. For example, referring to FIG. 6A, if the MR measurements indicate that the temperature increase at the target/non-target region is below a predetermined threshold (e.g., less than 0.5° C. between two consecutive measurements), the MR sequence controller may increase the time, $\Delta t$, associated with the gradient-field activity suppression (e.g., 5 ms between two RF excitations), thereby allowing longer or additional operations of the RF-sensitive measurement/treatment. The time period suppressing the MR gradient-field activity may be alternatively adjusted by the ultrasound controller 328 and/or the separate controller 340 as described above. The target and non-target regions may have the same or different predetermined thresholds; in addition, different types of non-target tissue may have different predetermined thresholds. If, however, the MR measurements indicate that the temperature increase at the target/non-target region exceeds a predetermined threshold (e.g., more than 1° C. between two consecutive measurements), the MR controller 326, ultrasound controller 328 and/or the separate controller 340 may reduce (or, in some embodiments, eliminate) the gradient-field suppression time for one or more pulses. For example, referring to FIG. 6B, the MR gradient-field activity may be suppressed every three MR gradient pulses, such that the RF-sensitive operation is performed once every three TRs. Alternatively, the gradient-field suppression time, $\Delta t$, between two RF excitations may be reduced (e.g., to 0.5 ms) as depicted in FIG. 6C.

In some embodiments, the location of the target region (and thereby its movement) is tracked using the MR measurements. For example, the target location on each MR image may be first identified using a suitable approach and the target movement between two consecutive image frames can then be determined. Similar to the approach described above, the repetition period of the MRI gradient pulses may be dynamically adjusted based on the target movement. For example, if the MR measurements indicate that the movement of the treatment target is below a predetermined threshold (e.g., 1 μm between two consecutive frames), the MR sequence controller may increase the time, $\Delta t$, associated with the gradient-field activity suppression so as to allow longer or additional operations of the RF-sensitive measurement/treatment. Likewise, if the MR measurements indicate that the movement of the treatment target exceeds a predetermined threshold (e.g., 10 μm between two consecutive frames), the gradient-field suppression time for one or more pulses may be reduced so as to closely track the movement of the treatment target.

Figure 6B:
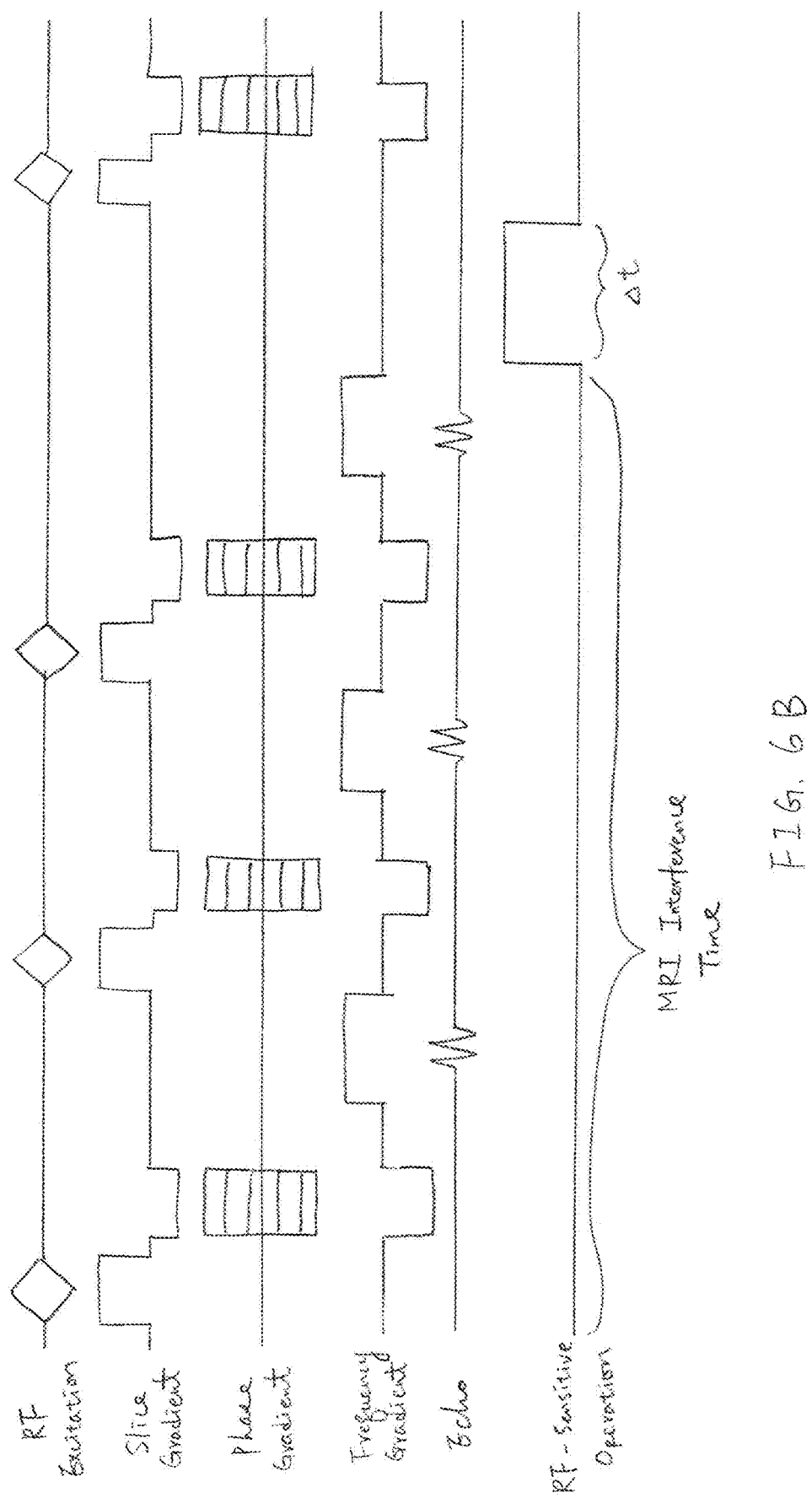

Alternatively or additionally, the gradient-field suppression period, $\Delta t$, may be adjusted based on the SNR of the reflection signals off the tissue interface and/or the cavitation signals. For example, if the SNR of the received signals is below a predetermined threshold, the MR controller 326, ultrasound controller 328 and/or the separate controller 340 may increase $\Delta t$ (as depicted in FIG. 6A), thereby allowing additional reflection/cavitation signals to be measured for increasing the measuring accuracy. If the SNR of the received signals exceeds the predetermined threshold, the gradient-field suppression period, $\Delta t$, may remain the same, or in some embodiments, may be reduced (as depicted in FIGS. 6B and 6C). Similarly, if a thermal map created by the MR apparatus indicates that the temperature in the target region achieves the desired treatment temperature and/or the temperature in the non-target region exceeds a predetermined threshold that is clinically intolerable, the MR controller 326, ultrasound controller 328 and/or the separate controller 340 may reduce or eliminate $\Delta t$ (as depicted in FIGS. 6B and 6C) such that less acoustic energy is delivered to target/non-target region within a certain period. If the temperature in the target region is below the desired treatment temperature, the gradient-field suppression period, $\Delta t$, may be increased to allow more acoustic energy to be delivered to the target (as depicted in FIG. 6A).

Figure 6D:
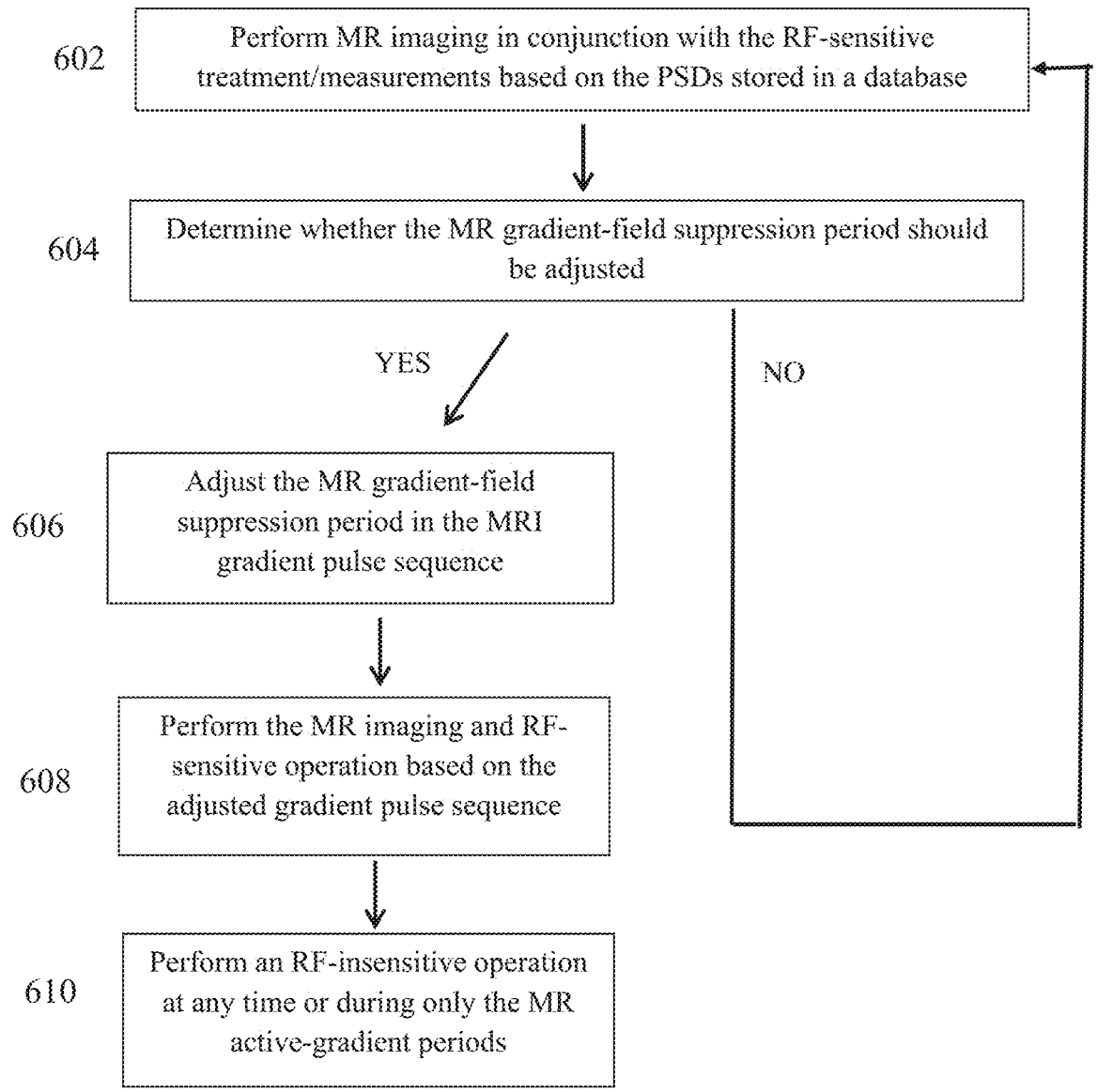
FIG. 6D is a flow chart illustrating an approach of dynamically adjusting a suppression time of MRI gradient-field activity in accordance with various embodiments.

Accordingly, various embodiments of the present invention advantageously allow the suppression time of the MR gradient-field activity to be dynamically adjusted based on the real-time measurements of the target movement, temperature increase at the target/non-target regions and/or reflection/cavitation signals. FIG. 6D illustrates dynamic adjustment of the MR gradient-field suppression period in accordance with various embodiments. In a first step 602, the MR imaging is performed in conjunction with the RF-sensitive treatment/measurements based on the PSDs stored in the database 324 using the approaches described above (e.g., in FIGS. 4B-4D). In step 604, information obtained by the MR apparatus 300, the ultrasound receiver 330 and/or the separate RF-noise receiver 332 are analyzed to determine whether the MR gradient-field suppression period should be adjusted. Based on this analysis, the MR controller 326, ultrasound controller 328 and/or the separate controller 340 may adjust the MR gradient-field suppression period in the MRI gradient pulse sequence (step 606). Thereafter, the MR imaging and RF-sensitive operation may be performed in accordance with the adjusted gradient pulse sequence using the approaches described above (e.g., in FIGS. 4B-4D) (step 608). If it is determined that there is no need to adjust the gradient-field suppression time, the MR imaging and RF-sensitive operation may be performed in accordance with the stored gradient pulse sequence. Again, the RF-insensitive ultrasound operations may be carried out (i) during only the MR active-gradient periods or (ii) at any time—i.e., during the MR active-gradient periods and/or the MR gradient-field-suppression periods (in step 606).

Although the present invention has been described with reference to an ultrasound transducer system and other specific details, it is not intended that such details should be regarded as limitations upon the scope of the invention. For example, systems and methods for synchronizing MR imaging with treatment modalities other than focused ultrasound therapy that include RF-sensitive operations are also included within the scope of the invention. Moreover, it is to be understood that the features of the various embodiments described herein are not necessarily mutually exclusive and can exist in various combinations and permutations, even if such combinations or permutations are not made express herein, without departing from the spirit and scope of the invention. In fact, variations, modifications, and other implementations of what is described herein will occur to those of ordinary skill in the art without departing from the spirit and the scope of the invention.

What is claimed is:

1. A system for performing a sequence of ultrasound operations of an anatomic region in conjunction with MR imaging of the region, the sequence of ultrasound operations comprising at least one RF-sensitive operation and at least one RF-insensitive operation, the system comprising:
   an MRI apparatus for imaging the anatomic region, the imaging comprising gradient field activity; and
   an ultrasound controller in communication with the MRI apparatus, the ultrasound controller (i) initiating the RF-insensitive operation at any time during the MR imaging and (ii) initiating the RF-sensitive operation in response to a signal indicative of the gradient-field-activity suppression,
   wherein the at least one RF-sensitive operation includes an operation associated with disturbance by RF excitement signals or the gradient-field-activity suppression, and the at least one RF-insensitive operation includes an operation which is not associated with disturbance by RF excitement signals or the gradient-field-activity suppression.

2. The system of claim 1, further comprising an MRI controller for operating the MRI apparatus in accordance with a pulse sequence that includes time intervals where the gradient field activity is suppressed, the signal being indicative of the time intervals.

3. The system of claim 1, further comprising an MRI controller for operating the MRI apparatus in accordance with a pulse sequence, the signal being indicative of an end of the pulse sequence.

4. The system of claim 3, wherein the ultrasound controller is further configured to trigger repetition of the pulse sequence after completion of the RF-sensitive operation.

5. The system of claim 1, further comprising an ultrasound apparatus for performing the sequence of ultrasound operations.

6. The system of claim 5, wherein the ultrasound apparatus comprises at least one of an ultrasound transducer, a cavitation detection device, or a reflection detection device, in communication with the ultrasound controller, for performing the RF-sensitive operation.

7. The system of claim 5, further comprising an MRI controller, wherein at least one of the ultrasound controller or the MRI controller is configured to adjust an MRI pulse sequence that includes time intervals where the gradient-field activity is suppressed based at least in part on information acquired using at least one of the MRI apparatus or the ultrasound apparatus.

8. The system of claim 7, wherein the MRI controller is further configured to operate the MRI apparatus in accordance with the adjusted MRI pulse sequence and the signal indicative of the gradient-field-activity suppression is based on the adjusted MRI pulse sequence.

9. The system of claim 7, wherein the information comprises at least one of a temperature increase at the anatomic region, a signal quality of reflections from the anatomic region, or a movement degree of the anatomic region.

10. The system of claim 1, further comprising a measurement system for measuring RF signals originating from the MRI apparatus, wherein the controller is further configured to perform the RF-sensitive operation based on the measured RF signals.

11. The system of claim 1, wherein the MRI apparatus comprises an MRI controller for transmitting the signal indicative of gradient-field-activity suppression to the ultrasound controller.

12. The system of claim 1, wherein the ultrasound controller is further configured to cause the gradient field activity to be periodically temporarily suppressed.

13. The system of claim 1, further comprising a system clock for synchronizing the RF-sensitive operation and MR imaging of the anatomic region.

14. A controller for synchronizing an MRI apparatus performing MR imaging, with an ultrasound system performing a sequence of ultrasound operations at least one of which is RF-sensitive operation and at least one of which is RF-insensitive operation, the controller comprising:
   a first module for receiving gradient-field-activity suppression information about an MRI pulse sequence specifying time intervals wherein gradient field activity is suppressed;
   a second module for (i) initiating the RF-sensitive ultrasound operation at an onset of the gradient-field-activity suppression based on the gradient-field-activity suppression information and (ii) initiating the RF-insensitive operation at any time during the MRI pulse sequence, wherein the RF-sensitive operation includes an operation associated with disturbance by RF excitement signals or the gradient-field-activity suppression, and the RF-insensitive operation includes an operation which is not associated with disturbance by RF excitement signals or the gradient-field-activity suppression.

15. An MRI system operable in conjunction with an ultrasound system for performing MR imaging of an anatomic region in conjunction with a sequence of ultrasound operations of the region, the sequence of ultrasound operations comprising at least one RF-sensitive operation and at least one RF-insensitive operation, the MRI system comprising:
   an MRI apparatus for imaging the anatomic region, the imaging comprising gradient field activity; and
   an MRI controller for operating the MRI apparatus in accordance with a pulse sequence that includes time intervals where the gradient field activity is suppressed, and signaling gradient-field-activity suppression information including the time intervals related to gradient-field-activity suppression to the ultrasound system so as to (i) cause performance of the RF-sensitive operation during the time intervals related to gradient-field-activity suppression (ii) cause performance of the RF-insensitive operation at any time during the pulse sequence of the MRI apparatus,
   wherein the at least one RF-sensitive operation includes an operation associated with disturbance by RF excitement signals or the gradient-field-activity suppression, and the at least one RF-insensitive operation includes an operation which is not associated with disturbance by RF excitement signals or the gradient-field-activity suppression.

16. An ultrasound system operable in conjunction with an MRI system for performing a sequence of ultrasound operations of an anatomic region in conjunction with MR imaging of the region, the sequence of ultrasound operations comprising at least one RF-sensitive operation and at least one RF-insensitive operation, the ultrasound system comprising:
- an ultrasound apparatus for performing the sequence of ultrasound operations; and
- an ultrasound controller for (i) initiating the RF-insensitive operation at any time during the MR imaging, (ii) initiating performance of the RF-sensitive operation in response to a signal indicative of gradient-field-activity suppression including an end of an MRI pulse sequence comprising gradient field activity, and (iii) triggering repetition of the pulse sequence after completion of the RF-sensitive operation,
- wherein the at least one RF-sensitive operation includes an operation associated with disturbance by RF excitement signals or the gradient-field-activity suppression, and the at least one RF-insensitive operation includes an operation which is not associated with disturbance by RF excitement signals or the gradient-field-activity suppression.

17. The ultrasound system of claim 16, wherein the ultrasound apparatus comprises an ultrasound transducer.

* * * * *